(12) United States Patent
Gonzalez-Sapienza et al.

(10) Patent No.: US 10,101,324 B2
(45) Date of Patent: Oct. 16, 2018

(54) NON-COMPETITIVE IMMUNOASSAYS TO DETECT SMALL MOLECULES USING NANOPEPTAMERS

(71) Applicants: The Regents of the University of California, Oakland, CA (US); Universidad de la República, Facultad de Química, Montevideo C.P, CA (US)

(72) Inventors: Gualberto Gonzalez-Sapienza, Montevideo (UY); Bruce Hammock, David, CA (US); Andres Gonzalez-Techera, Montevideo (UY); Lucia Vanrell, Montevideo (UY); Gabriel Lassabe, Canelones (UY)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 468 days.

(21) Appl. No.: 14/648,242

(22) PCT Filed: Nov. 26, 2013

(86) PCT No.: PCT/US2013/072028
§ 371 (c)(1),
(2) Date: May 28, 2015

(87) PCT Pub. No.: WO2014/088890
PCT Pub. Date: Dec. 6, 2014

(65) Prior Publication Data
US 2015/0309017 A1 Oct. 29, 2015

Related U.S. Application Data

(60) Provisional application No. 61/732,524, filed on Dec. 3, 2012.

(51) Int. Cl.
*G01N 33/53* (2006.01)
*G01N 33/543* (2006.01)

(52) U.S. Cl.
CPC .............................. *G01N 33/54306* (2013.01)

(58) Field of Classification Search
None
See application file for complete search history.

(56) References Cited

U.S. PATENT DOCUMENTS

| 6,165,750 A | 12/2000 | Stayton |
| 2008/0305559 A1 | 12/2008 | Gonzalez-Sapienza et al. |
| 2013/0102003 A1 | 4/2013 | Gibbs |

OTHER PUBLICATIONS

Vanrell, et al., "Nanopeptamers for the Development of Small-Analyte Lateral Flow Tests with a Positive Readout," *Anal. Chem.*, vol. 85, pp. 1177-1182 (2012).
International Search Report and Written Opinion for International Application No. PCT/US2013/072028 dated Jan. 30, 2014, 9 pages.

*Primary Examiner* — Gary Counts
(74) *Attorney, Agent, or Firm* — Mintz, Levin, Cohn, Ferris, Glovsky and Popeo, P.C.

(57) ABSTRACT

A method for noncompetitive detection of a small analyte using nanopeptamers, and devices useful for performing the methods. Nanopeptamers include a self-associating oligomeric protein that is attached to peptides that bind to an immune complex between the target analyte and a capture antibody. The noncompetitive methods allow for the direct detection of small analytes with increased sensitivity over competitive methods directed to the same target analyte, and provide a positive readout which is useful for rapid tests and on-site detection of small analytes such as such as pesticides, persistent organic pollutants, explosives, toxins, medicinal and abused drugs, and hormones.

21 Claims, 7 Drawing Sheets
Specification includes a Sequence Listing.

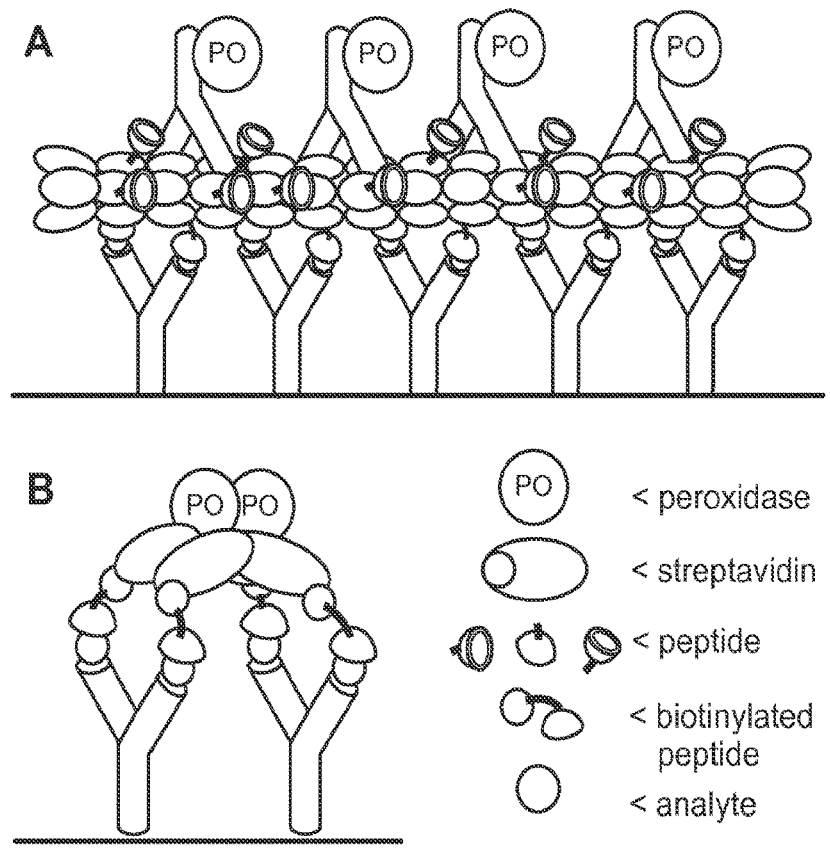
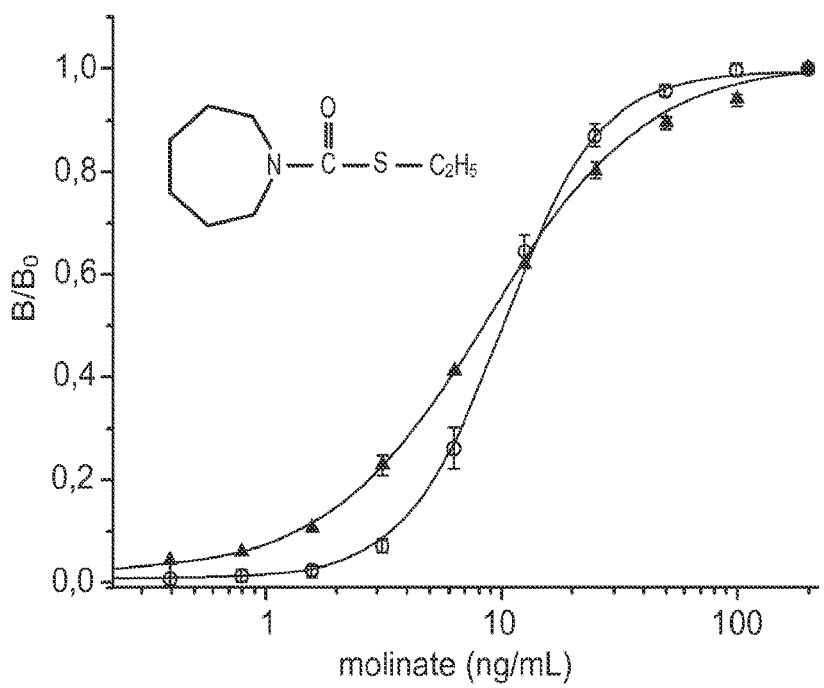
FIG. 2

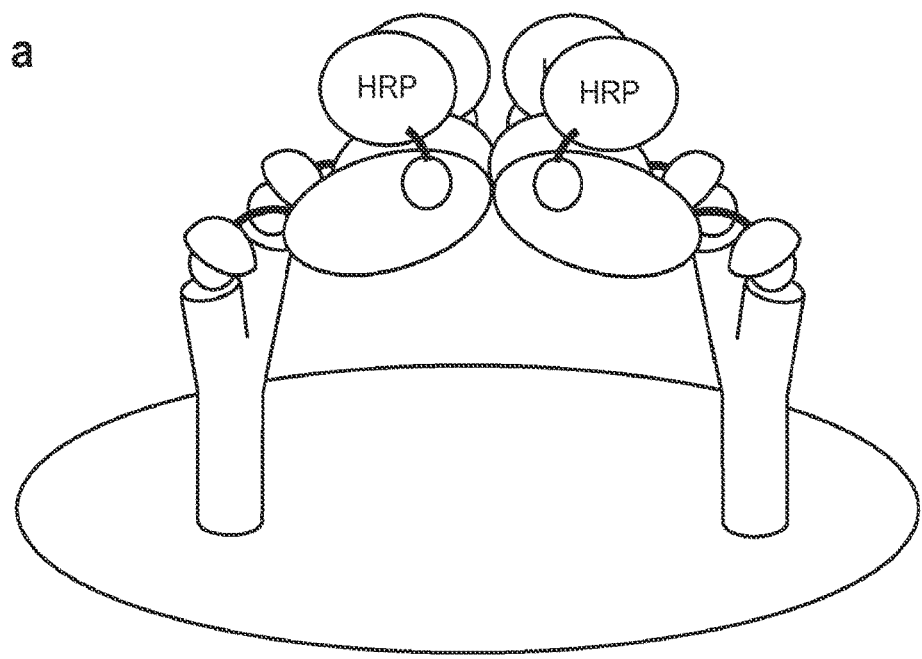
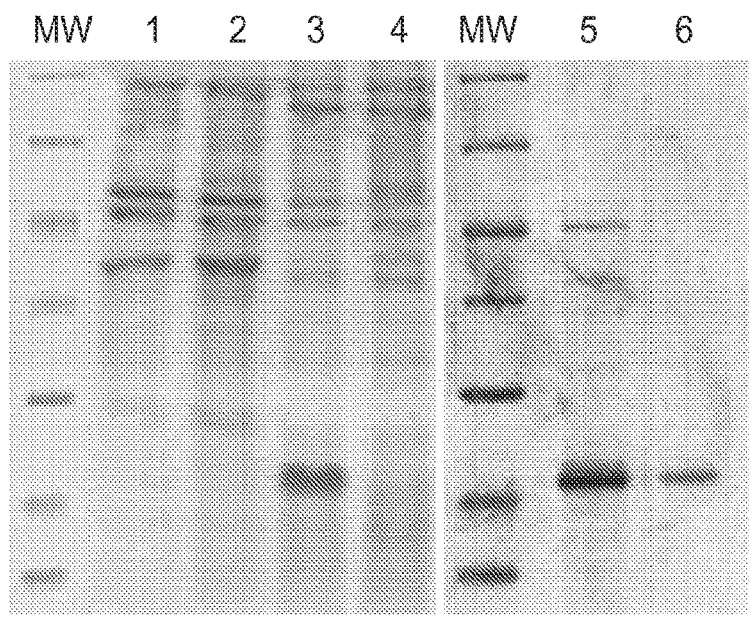
FIG. 7

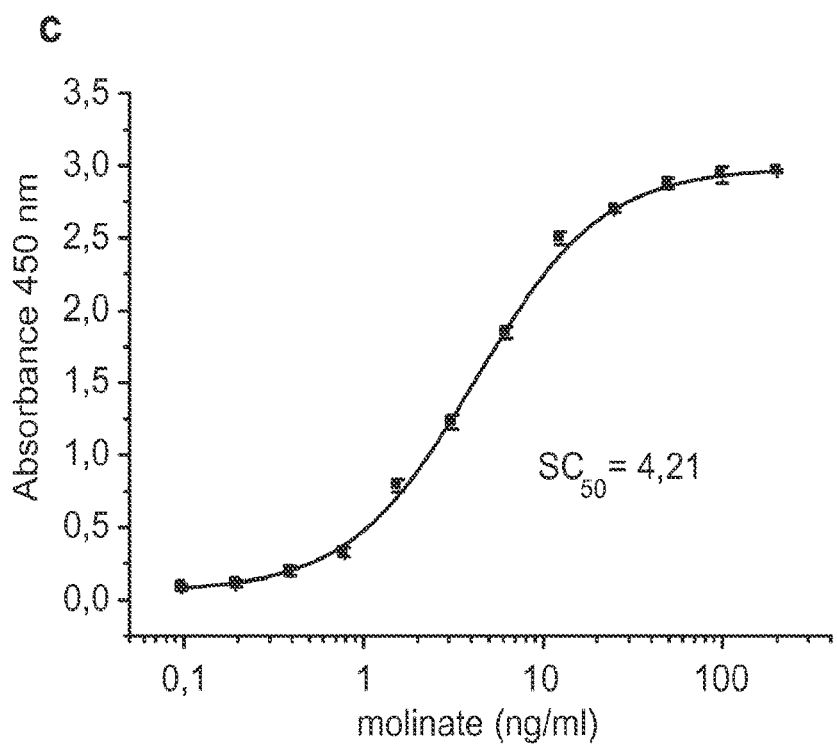
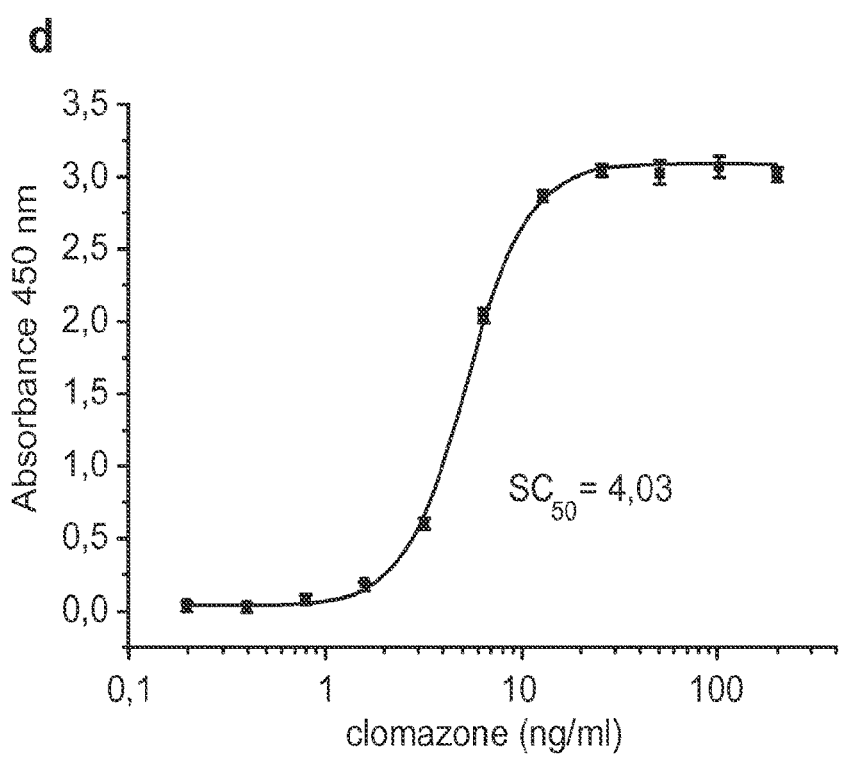
*FIG. 7*
(Continued)

a
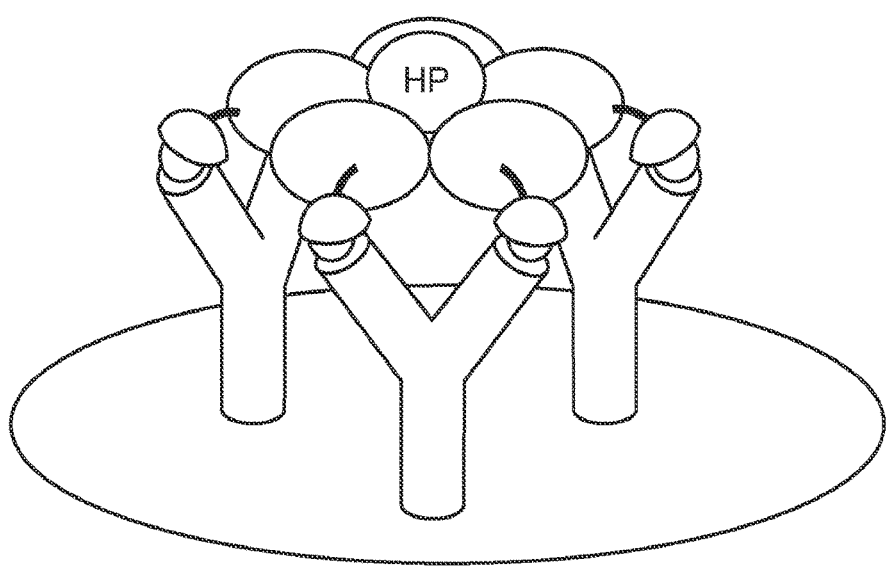
b
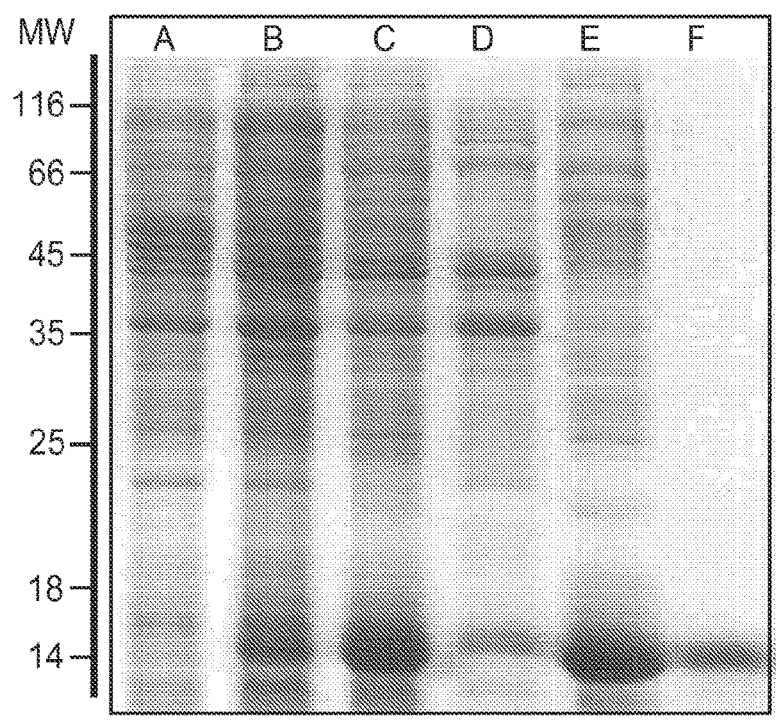
FIG. 8 c

Verotoxin - pA $SC_{50} = 5.41$ molinate (ng/ml)

Absorbance 450 nm d

Verotoxin - pA9

$SC_{50} = 0.10$

Atrazine (ng/ml)

Absorbance 450 nm

*FIG. 8*
(Continued)

NON-COMPETITIVE IMMUNOASSAYS TO DETECT SMALL MOLECULES USING NANOPEPTAMERS

CROSS-REFERENCES TO RELATED APPLICATIONS

The present patent application is the U.S. National Stage Entry under § 371 of International Application No. PCT/US2013/072028, filed Nov. 26. 2013, which claims benefit of priority to U.S patent application No. 61/732,524, filed Dec. 3, 2012, which is incorporated by reference herein in its entirety.

STATEMENT AS TO RIGHTS TO INVENTIONS MADE UNDER FEDERALLY SPONSORED RESEARCH AND DEVELOPMENT

This invention was made with government support under Grant No. TW005718 awarded by the National Institutes of Health. The government has certain rights in this invention.

BACKGROUND OF THE INVENTION

Due to their simplicity, speed, low cost and specificity, immunoassays have become useful tools for the analysis of a variety of biological substances and small compounds such as environmental pollutants. The vast majority of immunoassays for small analytes such as pesticides, industrial organic pollutants, microbial toxins, abused drugs, hormones, and pharmaceuticals etc., have a competitive format, i.e., once the anti-hapten antibodies are produced, the same hapten or a structurally related molecule is conjugated to a tracer enzyme for the competition with analyte for the binding sites of immobilized antibody or coating protein to capture free antibody in the competition with analyte. Competitive-format assays are inferior to noncompetitive formats for which immobilized antibody on the solid support captures target molecule and another antibody conjugated with a signaling molecule detects the captured molecule in terms of sensitivity, precision, kinetics and working range, and are more difficult to adapt to rapid "on site" or "clinic" assays, such as dipsticks or immunochromatography.

Traditional methods for developing immunoassays start with hapten synthesis and production of anti-analyte antibodies by immunization of animals with a hapten-protein conjugate. The hapten is typically an analyte related compound modified to be covalently conjugated to the carrier protein. Once an analyte-specific, high titer anti-hapten serum is obtained, a competitive immunoassay (e.g., an ELISA) can be developed by using the same hapten coupled to a unrelated carrier protein. When the same hapten is used for immunization and coating, the assay is designated as homologous ELISA. However, very frequently, homologous assays are less sensitive than heterologous assays (the hapten used for immunization and coating are different). The design of heterologous assays requires extensive chemical synthesis work in order to develop a proper panel of candidate haptens, which must afterwards be tested, to examine whether the desired sensitivity can be reached. For the detection of small molecules, a sandwich type noncompetitive ELISA format is not applicable because once antibody binds to the target molecule, there is no site available for the direct binding of secondary reporter antibody. Nevertheless, there have been efforts into the development of noncompetitive ELISA for small molecules and limited successes have been reported using anti-immunocomplex antibodies or recombinant antibody techniques. However, these methods require considerable time consuming and laborious procedures such as production of primary antibody against target molecule, reimmunization of analyte-antibody complex to obtain anti immunocomplex antibody, and screening of a panel of antibodies or generation of recombinant antibody library and successive screening to select the one with affinity for the analyte-antibody complex.

The compositions, methods and devices described herein provide improvements over current techniques for detecting small analytes, and allow the development of highly sensitive and specific assays for detecting small analytes in an easy to read noncompetitive format.

BRIEF SUMMARY OF THE INVENTION

The present invention is directed to methods and devices for detecting small analytes using noncompetitive assays, such as immunoassays. Thus, in one aspect, a method for the noncompetitive detection of a small analyte is provided. In order to detect the small analyte, the analyte is typically contacted with an antibody that specifically binds to the analyte, thereby forming an immune complex between the analyte and the antibody. The immune complex is then contacted with an affinity agent that specifically binds to the immune complex. The affinity agent comprises two components: a self-associated oligomeric protein and one or more peptides that are capable of specifically binding to the immune complex. The peptides are attached to the self-associated oligomeric protein, such that the self-associated oligomeric protein "displays" multiple copies of the peptide. The peptides typically comprise from about 5 to about 50 amino acids. The small analyte is detected by detecting binding of the affinity agent to the immune complex. The method is suitable for detecting analytes having a molecular weight of less than about 2500 daltons.

Thus, in one embodiment, the method comprises: (a) contacting at least one immune complex comprising an antibody specifically bound to the analyte, with an affinity agent comprising a self-associated oligomeric protein displaying multiple copies of a peptide, wherein at least one copy of the peptide specifically binds to the immune complex, and the peptide comprises from about 5 to about 50 amino acids; and (b) detecting the bound affinity agent, thereby detecting the analyte, where the analyte has a molecular weight of less than about 2500 daltons.

In some embodiments, the self-associated oligomeric protein is a homotetramer such as streptavidin or avidin. In one embodiment, the self-associated oligomeric protein is a homopentamer comprising the verotoxin 1 B-subunit. In one embodiment, the self-associated oligomeric protein is streptavidin, avidin or verotoxin. The self-associated oligomeric protein can be conjugated to a detectable label, such as an enzyme, a fluorescent label, a dye, or a magnetic particle.

The peptide displayed by the self-associated oligomeric protein can specifically bind to the analyte-antibody immune complex, but can have low specificity for the antibody alone. In some embodiments, the peptide specifically binds to both the analyte and the antibody of the immune complex. In some embodiments, the peptide comprises from about 5 to about 25 amino acids. In some embodiments, the peptide is obtained from a combinatorial biological library or a synthetic peptide library by selection with the analyte-antibody immune complex. The peptide can be attached to the self-associated oligomeric protein by non-covalent or covalent bonds.

The self-associated oligomeric protein can comprise a plurality of recombinant subunit monomers, where each monomer is linked to a copy of the peptide. The peptides can be directly linked to the recombinant subunit monomer by a peptide bond or indirectly linked to the subunit monomer by a spacer comprising amino acids.

The analyte can have a molecular weight of less than about 2500 daltons, or less that about 1000 daltons, or less than about 750 daltons, or less than about 500 daltons.

In some embodiments, the method further comprises contacting a sample suspected of containing the analyte with an antibody that specifically binds to the analyte, thereby forming the immune complex.

In another aspect, the present disclosure provides devices for performing the methods described herein. Thus, the device is capable of detecting a small analyte. In some embodiments, the device comprises (a) a solid support comprising an antibody that specifically binds to the analyte immobilized thereon; and (b) an affinity agent comprising a self-associated oligomeric protein displaying multiple copies of a peptide, the peptide comprising from about 5 to about 50 amino acids, wherein each peptide is capable of specifically binding to an immune complex formed when the antibody binds to the analyte, where the analyte has a molecular weight of less than about 2500 daltons.

The self-associated oligomeric protein of the device can be conjugated to a detectable label, such as an enzyme, a fluorescent label, a dye, or a magnetic particle. The detectable label can be detected by the human eye. In some embodiments of the device, the affinity agent is immobilized on the solid support.

BRIEF DESCRIPTION OF THE DRAWINGS

FIG. 1 shows the general structure scheme of PHAIA (phage anti-immunocomplex assay) and the Nanopeptamer noncompetitive assays. Panel A shows the scheme of PHAIA that typically uses filamentous M13 phage expressing disulfide constrained peptides (~100-200 copies along the ~2700 copies of the coat protein pVIII). Binding of the phage to the analyte-antibody immunocomplex is detected with an anti-M13 antibody coupled to horse radish peroxidase (PO). Panel B schematizes the substitution of the phage particle by a Nanopeptamer (a streptavidin conjugate, combined with four molecules of the biotynilated peptide).

FIG. 2 shows the results of noncompetitive nanopeptamer ELISAs for molinate using the peptides pA and p1M. MoAb 14D7 (10 ug/ml) was used to coat the wells of a microtiter plate and SPO (1.5 ug/ml) complexed with pA (triangles) or p1M (circles) was used for detection. The structure of molinate is shown in the inset.

FIG. 7 illustrates another embodiment of streptavidin-peptide nanopeptamers and their performance in noncompetitive ELISAs. a) Scheme of a streptavidin-peptide nanopeptamer recognizing its specific immunocomplex. In an ELISA format, analyte—antibody immunocomplex is recognized by the streptavidin-peptide nanopeptamer and the signal is obtained by adding biotinylated horse radish peroxidase (HRP). b) Streptavidin-pA nanopeptamer expression analysis by SDS/PAGE polyacrilamide gel stained with 0.1% coomassie blue. Lane 1: Soluble fraction of $E.\ coli$ B121 (DE3) transformed with the pET-OmpA encoding the streptavidin-pA chimera and grown in the presence of IPTG. Lane 2 : Soluble fraction of the same strain culture transformed as in 1) but grown without IPTG. Lane 3: Insoluble fraction of the same transformed strain grown in the presence of IPTG. Lane 4: Insoluble fraction of the same transformed strain grown without IPTG. Lane 5: Purified inclusion bodies of the transformed strain grown in the presence of IPTG. Lane 6: Purified streptavidin-pA chimera from inclusion bodies shown in 5. c) Noncompetitive streptavidin-pA nanopeptamer ELISA for molinate. MoAb14D7 (10 µg/mL) was used for coating, streptavidin-pA (5 µg/mL) was added in the presence of increasing molinate concentrations, and biotin-HRP was used for signal detection. The $SC_{50}$ obtained was 4.2 ng/mL. d) Noncompetitive streptavidin-pICX11 nanopeptamer ELISA for clomazone. MoAb5.6 (10 µg/mL) was used for coating, and streptavidin-pICX11 (5 µg/mL) was added in the presence of increasing clomazone concentrations. The $SC_{50}$ obtained was 4.0 ng/mL.

FIG. 8 illustrates another embodiment of nanopeptamers comprising verotoxin and peptides that recognize an immune complex, and their performance in noncompetitive ELISAs. a) Scheme of a verotoxin-peptide Nanopeptamer recognizing its specific immunocomplex. In an ELISA format, analyte—antibody immunocomplex is detected by the binding of the nanopeptamer coupled to horse radish peroxidase (HRP). b) Verotoxin-pA nanopeptamer expression analysis by SDS/PAGE and coomassie blue staining Lane A: *E. coli* B121 (DE3) cells. Lane B: *E. coli* B121 (DE3) transformed with the corresponding expression vector and grown without IPTG. Lane C: *E. coli* B121 (DE3) transformed with the corresponding expression vector grown in the presence of 100 mM IPTG. Lane D: soluble fraction of an *E. coli* B121 (DE3) culture grown as in C. Lane E: insoluble fraction of an *E. coli* B121 (DE3) culture grown as in C. Lane F: Soluble verotoxin-pA nanopeptamer after purification by affinity chromatography (using $Ni^{2+}$/EDTA HisTrap HP columns). c) Noncompetitive verotoxin-pA Nanopeptamer ELISA for molinate. MoAbl4D7 (10 μg/mL) was used for coating and verotoxin-pA (2 μg/mL) was added in the presence of increasing molinate concentrations. The $SC_{50}$ obtained was 5.41 ng/mL. d) Noncompetitive verotoxin-A9 nanopeptamer ELISA for atrazine. MoAbK4E7 (see Giersch, T., *A new monoclonal antibody for the sensitive detection of atrazine with immunoassay in microliter plate and dipstick format. J. Agric. Food Chem.,* 1993. 41 (6): p. 1006-1011) (5 μg/mL) was used for coating, and verotoxin-A9 (3.5 μg/mL) was added in the presence of increasing atrazine concentrations. The $SC_{50}$ obtained was 0.1 ng/mL.

DETAILED DESCRIPTION OF THE INVENTION

I. Introduction

The present invention provides non-competitive methods for detecting small analytes, and devices for performing the methods. The invention provides protein-multipeptide constructs referred to as nanopeptamers that are capable of specific binding to small analytes in a non-competitive two-site immunoassay format. The advantages of the methods and devices described herein include increased sensitivity, the development of assays for detecting small analytes having a positive instead of a negative readout, and the development of rapid point-of-use tests having a visually detectable readout that is easy to interpret. For example, the invention allows the development of novel non-competitive lateral flow assays and devices that produce an easy to detect visual readout when the small analyte is present in a sample.

II. Definitions

"Analyte" refers to a compound whose presence or absence is to be detected. A "small analyte" or "small molecule" as used herein is an analyte having a molecular weight of less than about 2500 daltons, or less than about 1000 daltons, or less than about 750 daltons, or less than about 500 daltons. Small analytes include, e.g., pesticides, industrial organic pollutants, microbial toxins, drugs (e.g., illegal drugs such narcotics), hormones, explosives, dyes, and plasticizers.

"Non-competitive detection of a small analyte" refers, in general, to an assay in which a target analyte is detected using two different binding molecules, such as antibodies or peptides. The first binding molecule (e.g., an antibody) is specific for the analyte alone, whereas the second binding molecule (e.g., a peptide) is specific for the complex formed between the first binding molecule and the target analyte. In particular, the term refers to an assay in which an immune complex comprising an antibody bound to a target analyte of interest is contacted with an affinity agent as described herein. The analyte is detected using a detectable label that binds to the affinity agent or the immune complex.

"Immune complex" refers to a complex formed between an analyte and an antibody molecule, or functional fragment thereof, that specifically binds the analyte. The complex is generally a non-covalent association between the analyte and antibody.

"Sample" refers to a composition from any source which is suspected of containing a small analyte of interest. The samples can be tested by the methods described herein and include, e.g., water from an ocean, lake, river, pond, or stream, runoff water from an agricultural field, waste stream from an industrial operation (e.g., a mine, a heating plant, or a manufacturing plant) cosmetics, human food, or nutraceuticals. A sample can be from a laboratory source or from a non-laboratory source. A sample may be suspended or dissolved in liquid materials such as buffers, extractants, solvents and the like. Samples also include animal and human body fluids such as whole blood, blood fractions, serum, plasma, cerebrospinal fluid, lymph fluids, milk; and biological fluids such as tissue and cell extracts, cell culture supernatants; fixed tissue specimens; and fixed cell specimens.

"Antibody" refers to a polypeptide encoded by an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Antibodies are representative of a wide variety of receptors including hormone receptors, drug targets such as peripheral benzodiazepine receptor, and carrier proteins.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively. Some animals (such as camelids and sharks) also produce single chain antibodies devoid of light chains. In these antibodies the single N-terminal domain (VHH) is fully capable of antigen binding (see, e.g. Hamers-Casterman et al., Nature 363:446-448 (1993), Greenberg et al. Nature 374:168-173 (1995)).

Antibodies exist, e.g., as intact immunoglobulins or as a number of well-characterized fragments produced by digestion with various peptidases. Thus, for example, pepsin digests an antibody below the disulfide linkages in the hinge region to produce F(ab')2, a dimer of Fab which itself is a light chain joined to VH—CH1 by a disulfide bond. The F(ab')2 may be reduced under mild conditions to break the disulfide linkage in the hinge region, thereby converting the F(ab')2 dimer into an Fab monomer. The Fab monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

For preparation of monoclonal or polyclonal antibodies, any technique known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985)). Techniques for the production of single chain antibodies (see U.S. Pat. No. 4,946,778) can be adapted to produce antibodies to analytes. Also, transgenic mice, or other organisms, such as other mammals, may be used to express humanized antibodies. Alternatively, phage display technology can be used to identify antibodies, heteromeric Fab fragments and other proteins that specifically bind to selected antigens and/or analytes of interest (see, e.g., McCafferty et al., Nature 348:552-554 (1990); Marks et al., Biotechnology 10:779-783 (1992)).

"Specifically (or selectively) binds," when referring to an antibody, refers to a binding reaction that is determinative of the presence of the antibody's binding target (e.g., a small analyte) in a heterogeneous population of analytes (e.g., small molecules, proteins and other antigens). Thus, under designated immunoassay conditions, the specified antibodies bind to their binding target at least two times the background and do not substantially bind in a significant amount to other analytes present in the sample. Specific binding to an antibody under such conditions may require an antibody that is selected for its specificity for a particular target (e.g., a small analyte, an oligomeric protein or a fusion protein). For example, monoclonal and polyclonal antibodies raised to fusion proteins can be selected to obtain only those monoclonal and polyclonal antibodies that are specifically immunoreactive with a fusion protein and not with individual components of the fusion proteins. Selection may be achieved by subtracting out antibodies that cross-react with the individual antigens or analytes. A variety of immunoassay formats may be used to select antibodies specifically immunoreactive with a particular target (e.g., a small analyte or an oligomeric protein). For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background. Specific monoclonal antibodies will usually bind with a $K_D$ of at least about $10^{-8}$ M, more usually at least about $10^{-10}$ M; and most preferably, about $10^{-12}$ M or better.

Figure 3:
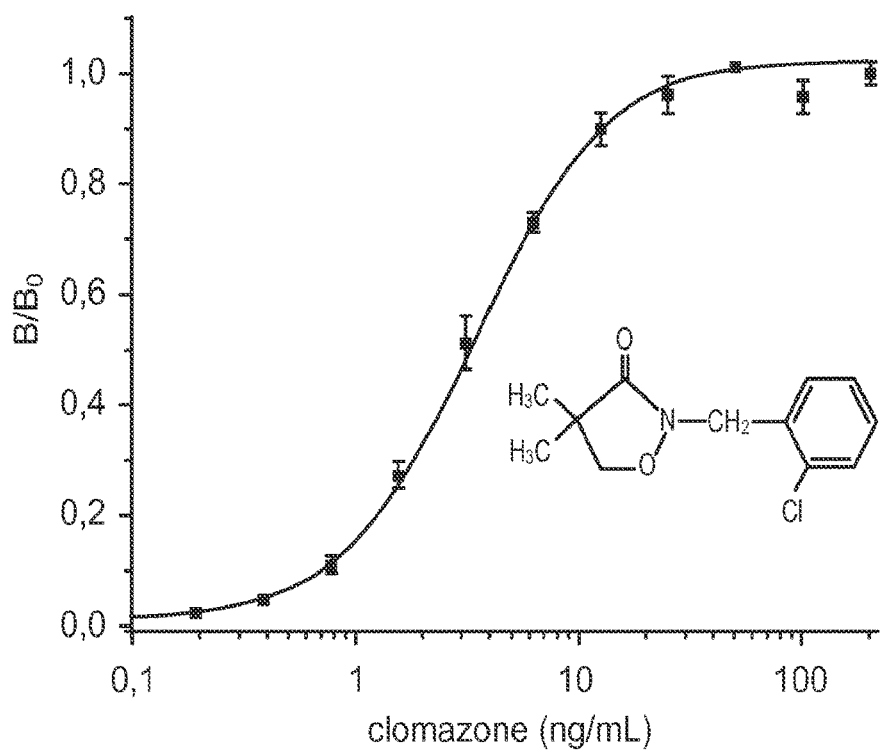
FIG. 3 shows the results of noncompetitive nanopeptamer ELISAs for clomazone using the peptide pX11. MoAb 5.6 (10 ug·ml) was used for coating and anti-clomazone IC pX11-nanopeptamer was assayed using the conditions described above in the legend for FIG. 2 for molinate. The structure of clomazone is shown in the inset.

"Sensitivity" refers to the ability of an assay to detect a target analyte above the zero signal or background level, and for non-competitive assays can be expressed as the midpoint corresponding to the concentration of analyte giving 50% of signal saturation ($SC_{50}$). Sensitivity can also be expressed as the limit of detection (LOD), which is defined as the analyte concentration giving a 10% increase over the zero or background signal, or as the analyte concentration producing a signal equal to that of the background plus three standard deviations.

"Specifically binds the immune complex" refers to specific binding of a peptide such that the peptide reacts with measurable affinity with the immune complex, but reacts with much lower or negligible affinity with the uncomplexed antibody, when the peptide is part of an affinity agent described herein. For example, the peptide can bind the immune complex with at least 1, 2, 3, 4, 5, 6, 7, 8, 9, or 10-fold higher affinity than to the uncomplexed antibody, when the peptide is part of an affinity agent described herein.

"Affinity agent" refers to an oligomeric protein that is attached to or "displays" a plurality of peptides, where each of the peptides is capable of specific binding to an antibody-analyte immune complex. The oligomeric protein can be a monomer, dimer, trimer, tetramer, pentamer, hexamer, heptamer, octamer, nonamer, and so on. The displayed peptides can be the same or different peptides.

"Self-associated oligomeric protein" refers to a protein comprising subunits or monomers that are capable of self-associating into a protein having an oligomeric quaternary structure. The subunits can be the same or different. For example, the self-associated oligomeric protein can comprise two, three, four, five, six, seven, eight, nine, or more subunits. "Subunit monomer" refers to a protein or polypeptide that comprises one component of an oligomeric protein complex. Subunit monomers typically associate into oligomeric quarternary structures by non-covalent attachments.

"Protein displaying multiple copies of a peptide" refers to any configuration by which one or more copies of a peptide described herein are attached to a protein, such as a self-associated oligomeric protein. For example, the peptides can be attached to the protein by covalent or non-covalent bonds. The peptides can be attached to the N-terminus, carboxy-terminus, or both, of the protein. The peptides can also be conjugated to the protein. The peptides can be directly attached to the protein, or indirectly attached, e.g., by using a spacer molecule.

"Peptide" refers to a polymer of amino acids joined by peptide bonds. As used herein, the term peptide is distinct from the term "protein." For example, a peptide has from about 5 to about 50 amino acids. Thus, for purposes of this disclosure, a peptide is not a protein.

"Protein or "polypeptide" refers to a polymer of amino acid residues. The protein can comprise naturally occurring amino acids, non-natural amino acids, or a combination of both. The term protein as used herein typically refers to polypeptides, normally having more than 50 residues, that fold into unique stable 3-dimensional structures.

"Streptavidin" is a tetrameric protein that binds biotin with high affinity. Streptavidin is composed of four identical subunits. The 159 amino acid full-length protein subunit of streptavidin is processed to produce a "core" subunit that generally comprises residues 13-139. Removal of the N and C termini is necessary for high affinity binding to biotin. Each streptaviding monomer comprises an antiparallel beta-barrel tertiary structure, with a biotin binding site at one end of each beta-barrel. Four identical streptavidin monomers associate to produce a tetrameric quaternary structure (an oligotetramer).

"Avidin" is a tetrameric protein that binds biotin with high affinity, and has similar structure to streptavidin.

"Selection with the analyte-antibody immune complex," in the context of a peptide library, refers to contacting the members of peptide library with an antibody-small analyte immune complex (IC) and determining which peptide sequence binds to the IC. The peptide that binds the IC of interest is then separated and recovered from peptides that do not bind the IC, and the identity (i.e., the amino acid sequence) of the peptide is determined.

"Non-covalent attachment" or "non-covalent bond" refers to an interaction between two molecules, such as a protein and a peptide, that does not involve the sharing of electron pairs. Non-covalent interactions include attractive intermolecular forces such as ionic bonds, hydrophobic interactions, hydrogen bonds, and van der Waals forces.

"Covalent attachment" or "covalent bond" refers to a chemical bond that involves the sharing of electron pairs between atoms.

"Peptide bond" refers to a covalent chemical bond between two molecules, such as amino acids, where the carboxyl group of one molecule reacts with the amino group of the other molecule producing a C(O)NH bond.

"Spacer" or "linker" refers to a group of amino acids that connect a non-polypeptide moiety, such as biotin, to a peptide or protein, or connects two proteins, two peptides, or a protein and a peptide, for example, in a fusion protein. The spacer can be attached to the protein and/or peptide via a covalent or peptide bond. A spacer comprising a peptide bond can be encoded by a nucleic acid molecule, e.g., a nucleic acid molecule that encodes a fusion protein, or can be synthesized as part of a protein or peptide.

"Fusion protein" refers to a protein containing amino acid sequences from heterologous proteins or peptides that are joined by covalent bonds or peptide bonds to yield a functional protein. The term "heterologous" when used with reference to a protein indicates that the protein comprises two or more subsequences that are not found in the same relationship to each other in nature (e.g., a fusion protein between an oligomeric protein subunit monomer and a peptide that specifically binds to an antibody-small analyte immune complex). The fusion protein can comprise a spacer or linker between the heterologous sequences.

"Conjugated" refers to linking a molecule or moiety to a protein or peptide. For example, a detectable label can be conjugated to an antibody or an oligomeric protein, or biotin can be conjugated to a peptide of the invention. Methods of conjugating molecules to proteins are well known in the art, and include using a reactive cysteine linker.

"Detectable label" refers to a material having a detectable physical or chemical property. Thus, a label is any composition detectable by spectroscopic, photochemical, biochemical, electrical, optical or chemical means. Examples of detectable labels include dyes, radioactive isotopes, enzymes that produce detectable products from substrates, etc.

"Dye" refers to a compound that is detectable as a color, including black, that can be used to label a protein, antibody, or other molecule. Dyes can be visible to the unaided human dye, or can be visible when excited by certain wavelengths of light, such a fluorescent dyes.

"About," when modifying any amount, refers to the variation in that amount typically encountered by one of skill in the art. For example, the term "about" refers to the normal variation encountered in measurements for a given analytical technique, both within and between batches or samples. Thus, the term about can include variation of 1-10% of the measured value, such as 5% or 10% variation. The amounts disclosed herein include equivalents to those amounts, including amounts modified or not modified by the term "about."

III. Methods of the Invention

The present invention provides noncompetitive methods for detecting a small analyte. In some embodiments, the method comprises a noncompetitive immunoassay for detecting small analytes. Antibodies that specifically bind to a small analyte of interest (e.g., a pesticide, an industrial organic pollutants, a microbial toxin, a hormone, or a drug, including, e.g., illegal drugs such as narcotics) are contacted with a sample suspected of containing the small analyte. If present, the small analyte forms an immune complex with the antibody. The complex is then contacted with an affinity agent (e.g., a nanopeptamer) as described herein. The bound affinity agent is detected, thereby detecting the small analyte.

A. Immune Complex

The methods described herein detect an analyte that is part of an immune complex. The complex formed by specific binding of the analyte to an antibody is referred to as an immune complex. Analytes that are detectable by the methods of the invention are described below.

1. Analytes

The present invention provides methods and compositions for detecting an analyte. The methods and compositions are particularly useful for detecting small analytes, such as pesticides, organic pollutants, explosives, toxins, medicinal and abused drugs, hormones, and the like. Thus, in some embodiments, the analyte that is detected has a molecular weight of less that about 2500 daltons, less than about 2000 daltons, less than about 1500 daltons, less than about 1000 daltons, less than about 900 daltons, less than about 800 daltons, less than about 700 daltons, less than about 600 daltons, less than about 550 daltons, or less than about 500 daltons.

Non-limiting examples of analytes that can be detected by the methods and devices described herein include, e.g., pesticides, industrial organic pollutants, microbial toxins, drugs (e.g., illegal drugs such narcotics), hormones, explosives, dyes, and plasticizers. Industrial organics include polyhalogenated biphenyls, dioxins, dibenzofurans, aromatic ethers, ureas, aromatic amines, and may other pyrethroids. Pesticides include, e.g., thiocarbamates, phosphate esters, thiophosphates, carbamates, polyhalogenated sulfonamides, and their metabolites and derivatives. Drugs include, e.g., alkaloids such as morphine alkaloids such as, for example, morphine, codeine, heroin, dextromethorphan, cocaine alkaloids, such as, e.g., cocaine and benzoylecgonine; ergot alkaloids, which include the diethylamide of lysergic acid; steroid alkaloids; iminazoyl alkaloids; quinazoline alkaloids; isoquinoline alkaloids; quinoline alkaloids, which include quinine and quinidine; diterpene alkaloids; lactams including, e.g., barbiturates such as, phenobarbital and secobarbital, diphenylhydantoin, primidone, ethosuximide; aminoalkylbenzenes, including, e.g., amphetamines; catecholamines such as ephedrine, L-dopa, epinephrine; narceine; papaverine; and their metabolites; benzheterocyclics, including, e.g., oxazepam, chlorpromazine, tegretol, their derivatives and metabolites; purines, including, e.g., which theophylline and caffeine; drugs derived from marijuana, including, e.g., cannabinol and tetrahydrocannabinol; polypeptides such as angiotensin, LHRH, and immunosuppresants such as cyclosporin, prograf, digosin, FK506, mycophenolic acid, and the like; vitamins such as A, B, e.g. B12, C, D, E and K, folic acid, thiamine; prostaglandins; tricyclic antidepressants, which include imipramine, dismethylimipramine, amitriptyline, nortriptyline, protriptyline, trimipramine, chlomipramine, doxepine, and desmethyldoxepin; anti-neoplastics, including, e.g., methotrexate; antibiotics, including, e.g., penicillin, chloromycetin, actinomycetin, tetracycline, terramycin. Hormones include, e.g., thyroxine, cortisol, triiodothyronine, testosterone, estradiol, estrone, progestrone, steroids, including, e.g., estrogens, androgens, andreocortical steroids, bile acids, cardiotonic glycosides and aglycones, which includes digoxin and digoxigenin, saponins and sapogenins, and steroid mimetic substances, such as diethylstilbestrol. Explosives include, e.g., 2, 4, 6 trinitrotoluene and a wide variety of alkyl and arynitro compounds.

2. Antibodies that Specifically Bind Small Analytes

In order to detect the analyte, one needs an antibody that specifically binds the analyte in a sample. The antibody that binds the analyte is sometimes referred to as a capture antibody. For preparation of antibodies that specifically bind the target analyte, e.g., recombinant, monoclonal, or polyclonal antibodies, any technique known in the art can be used (see, e.g., Kohler & Milstein, Nature 256:495-497 (1975); Kozbor et al., Immunology Today 4: 72 (1983); Cole et al, pp. 77-96 in Monoclonal Antibodies and Cancer Therapy, Alan R. Liss, Inc. (1985); Coligan, Current Protocols in Immunology (1991); Harlow & Lane, supra; and Goding, Monoclonal Antibodies: Principles and Practice (2d ed. 1986)). Generation and screening of antigen specific polyclonal antibodies is described in, e.g., Harlow and Lane, supra. Generation of monoclonal antibodies has been previously described and can be accomplished by any means known in the art. (see, e.g., Buhring et al. in Hybridoma 1991, Vol. 10, No. 1, pp. 77-78). Anti-analyte antibodies can be produced by immunizing animals with an analyte-protein conjugate. For example, an animal such as a guinea pig or rat, preferably a mouse, is immunized with a small analyte conjugated to a hapten (e.g., KLH), the antibody-producing cells, preferably splenic lymphocytes, are collected and fused to a stable, immortalized cell line, preferably a myeloma cell line, to produce hybridoma cells which are then isolated and cloned. (see, e.g., U.S. Pat. No. 6,156,882). Generation of monoclonal antibodies against small analytes has been described in, e.g., Rufo et al., J. Ag. Food Chem. 52:182-187 (2004). Small compounds or analytes typically bind to hydrophobic pockets that form at the interface of the heavy and light chain variable domains and up to 85% of their surface can be buried (see e. g., Lamminmaki et al., J. Biol. Chem. 39:36687-94 89 (2001); Monnet et al., J. Mol. Bio. 315:699-712 (2002)). In addition, the genes encoding the heavy and light chains of a small analyte-specific antibody can be cloned from a cell, e.g., the genes encoding a monoclonal antibody can be cloned from a hybridoma and used to produce a recombinant monoclonal antibody. Specific monoclonal antibodies will usually bind with a $K_D$ of at least about $10^{-8}$ M, more usually at least about $10^{-10}$ M; and most preferably, about $10^{-12}$ M or better.

B. Affinity Agents

In order to detect a small analyte described herein, an affinity agent is used. The affinity agent is capable of specifically binding to the immune complex formed between a capture antibody and the target analyte of interest. The affinity agent comprises a self-associated oligomeric protein that is attached to or "displays" multiple copies of a peptide that binds to an immune complex. For example, the affinity agent can display two, three, four, five, six, seven, eight, nine, or more peptides. The affinity agent is sometimes referred to herein as a nanopeptamer.

In some embodiments, the affinity agent comprises multiple copies of a peptide conjugated to a nanoparticle such as a bead, liposome, or other core scaffold that displays the peptides.

1. Self-Associated Oligomeric Proteins

The affinity agent comprises a self-associated oligomeric protein that displays multiple copies of a peptide, where each peptide is capable of binding to the immune complex, thereby increasing the avidity of the binding interactions. The self-associated oligomeric protein typically comprises multiple subunits or monomers that are capable of assembling into a protein complex. The monomeric subunits can spontaneously self-associate to form oligomeric proteins. The subunits can be the same (i.e., identical or substantially identical to each other), in which case the oligomeric protein is a homo-oligomeric protein. The subunits can also be different from each other, in which case the oligomeric protein is a hetero-oligomeric protein.

In some embodiments, four identical monomeric subunits self-associate to form a homotetrameric protein. Thus, in one embodiment, the subunit is a so-called "core" streptavidin subunit, and the subunits associate to form a streptavidin protein having a tetrameric quaternary structure. In other embodiments, the subunit is an avidin subunit, and the avidin subunits self-associate to form a avidin protein having a tetrameric quaternary structure.

In some embodiments, five identical monomeric subunits self-associate to form a homopentameric protein. Thus, in one embodiment, the subunit is a verotoxin 1 B-subunit, and five B-subunits associate to form a homopentameric verotoxin 1 B-subunit protein. In some embodiments, the self-associated oligomeric protein is streptavidin, avidin, or verotoxin. As will be understood by one of skill in the art, other combinations of subunits using monomers from other proteins are possible, as long as the subunits are capable of self-associating to form an oligomeric protein.

2. Peptides that Specifically Bind to Antibody-Analyte Immune Complexes

The affinity agent also comprises a peptide that is attached to or otherwise displayed by the oligomeric protein of the affinity agent. The peptide can comprise from about 5 to about 50 amino acids, or from about 5 to about 40 amino acids, or from about 5 to about 30 amino acids, or from about 5 to about 25 amino acids, or from about 5 to about 20 amino acids, or from about 5 to about 15 amino acids, or from about 10 to about 25 amino acids, or from about 10 to about 20 amino acids, or from about 10 to about 15 amino acids. As understood by one of skill in the art, the peptides described herein are distinct from antibodies or fragments thereof, ligands, and other proteins that can be used to bind to an immune complex. Thus, the peptides of the invention are not proteins as that term is used herein.

The peptides described herein are selected for specific and/or high affinity binding to the antibody-analyte immune complex (IC). In particular, the peptides of the affinity agent can be selected for specific binding to the hapten binding pocket of the capture antibody after analyte binding. For example, peptides can be selected that specifically react with the exposed region of the analyte and the conformational changes in the capture antibody caused by its binding. Thus, in some embodiments, peptides are selected that specifically bind to both the analyte and the antibody of the IC. The peptides described herein typically have low specificity and/or low affinity binding to the capture antibody alone. In some embodiments, the peptide is p1M, pA, pICX11, or pA9.

Peptides having the desired characteristics can be selected by any means known in the art. For example, the peptides described herein can be identified using phage display technology (see, e.g., Cardozo et al., Env. Sci. Tech. 39(100):4234 (2005); Goldman et al., Analytica Chimica Acta 457:13-19 (2002); McCafferty et al., Nature 348:552-554 (1990); Marks et al., Biotechnology 10:779-783 (1992)). Phage display peptide libraries are reviewed by Smith and Petrenko (see, e.g., Smith, G. P. and V. A. Petrenko, Phage Display. Chem. Rev, 1997, 97(2): p. 391-410). A phage display system is a system in which peptides of interest are expressed as fusion proteins on the phage surface (Pharmacia, Milwaukee Wis.). Phage display can involve the presentation of a peptide sequence that specifically binds to a complex between an antibody and a small molecule on the surface of a filamentous bacteriophage, typically as a fusion with a bacteriophage coat protein (e.g., pVIII or pIII). Methods for selecting peptides that bind immune complexes comprising a small analyte and a capture antibody using phage display are described in US patent publication 2008/0305559, which is incorporated by reference herein.

The peptides of the present invention can be chemically synthesized using conventional peptide synthesis or other protocols well known in the art. Peptides can be synthesized by solid-phase peptide synthesis methods using procedures similar to those described by Merrifield et al, J. Am. Chem. Soc, 85:2149-2156 (1963); Barany and Merrifield, Solid-Phase Peptide Synthesis, in The Peptides: Analysis, Synthesis, Biology Gross and Meienhofer (eds.), Academic Press, N. Y., vol. 2, pp. 3-284 (1980); and Stewart et al, Solid Phase Peptide Synthesis 2nd ed., Pierce Chem. Co., Rockford, 111. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl)phenoxy resin; tert-alkyloxycarbonyl-hydrazidated resins, and the like. Such resins are commercially available and their methods of preparation are known by those of ordinary skill in the art. Briefly, the C-terminal N-α-protected amino acid is first attached to the solid support. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Details of appropriate chemistries, resins, protecting groups, protected amino acids and reagents are well known in the art and so are not discussed in detail herein (See, e.g., Atherton et al, Solid Phase Peptide Synthesis: A Practical Approach, IRL Press (1989), and Bodanszky, Peptide Chemistry, A Practical Textbook, 2nd Ed., Springer-Verlag (1993)).

In some embodiments, the peptides are obtained from other combinatorial biological peptide libraries, such as yeast, bacterial, o ribosome display, by selection for specific binding to the analyte-antibody immune complex. Combinatorial biological peptide libraries are described in Benhar, Biotechnol. Adv. 19:1-33 (2001); Thom et al., Methods Mol. Biol. 901:101-116 (2012).

In some embodiments, the peptides are obtained from a synthetic peptide library by selection for specific binding to the analyte-antibody immune complex. Synthetic peptide libraries are described in Lam et al., Chem. Rev. 97:411-448 (1997).

C. Peptide Display

In order to bind with high avidity to the small analyte-antibody immune complex, the peptides described herein are displayed by the self-associated oligomeric protein of the affinity agent. The peptides are displayed by attaching the peptide to the oligomeric protein by either non-covalent or covalent bonds. The peptides can also be displayed by conjugating the peptides (via covalent or non-covalent bonds) to a solid-support such as a nanoparticle or bead, or to a liposome or other suitable core structure.

1. Non-Covalent Attachment

In some embodiments, the peptide is non-covalently attached to the self-associated oligomeric protein. For example, the peptide can be conjugated to a molecule that binds with high affinity to the oligomeric protein. Thus, in some embodiments, the oligomeric protein is avidin or streptavidin and the peptide is conjugated to biotin. The biotinylated peptide binds with high affinity to the tetrameric avidin or streptavidin molecule. Because each tetramer of avidin or streptavidin binds four biotin molecules, the affinity agent can comprise four biotinylated peptides.

Methods for conjugating peptides to biotin are well known in the art. The chemical reactions can involve any active group as long as it does not affect the binding activity of the peptide. Examples of suitable chemical reactions for conjugating peptides to biotin include reactions involving maleimides or iodoacetyl groups.

Alternatively, when chemical conjugation is not feasible or is not desired, a linker can be used. A linker can be attached to the N- or C-terminus of the peptide. The linker can comprise a covalent bond such as a peptide bond or a disulfide bond. Alternatively, a variety of other linkers with appropriate functional groups such as carbon linkers (e.g., straight or branched-chain carbon linkers, heterocyclic carbon linkers) or polyether linkers can be used to practice the present invention. These linkers may be joined to a peptide's constituent amino acids through their side groups (for example, through a disulfide linkage to cysteine). The linkers may also be joined to the a-carbon amino or carboxyl groups of the peptide's terminal amino acids.

2. Covalent Attachment

In some embodiments, the peptide is covalently attached to the self-associated oligomeric protein. For example, the covalent bond can be a peptide bond. Thus, the peptide can be attached to the self-associated oligomeric protein by a peptide bond. In some embodiments, the self-associated oligomeric protein comprises a plurality of subunit monomers each linked to a copy of the peptide. The subunit monomer can be linked to the peptide by a peptide bond. In one embodiment, the subunit monomer is linked to the peptide by a spacer comprising at least one amino acid.

Other examples of covalent bonds include disulfide bonds that can be used to join cysteine residues in the oligomeric protein and peptide, and thereby attach the peptide to the oligomeric protein.

3. Fusion Proteins

One way to display the peptides of the invention is to generate a fusion protein comprising a subunit of the oligomeric protein and the peptide. The fusion protein can be synthesized using peptide synthesis techniques described above. Alternatively, the fusion protein can be a recombinant fusion protein that is translated from a nucleic acid template encoding the fusion protein. The nucleic acid template comprises nucleic acid sequences that encode both the oligomeric protein subunit and the peptide. Translation of the template results in a fusion protein comprising the oligomeric protein and peptide joined by peptide bonds. The template can further comprise nucleic acid sequences that encode a spacer sequence of amino acids that are translated in frame with the fusion protein. The nucleic acid template can be inserted into an expression vector containing nucleic acid regulatory sequences that direct transcription and/or translation of the fusion protein encoded by the template. For example, the expression vector can contain enhancer, promoter, ribosomal binding site, and transcription and/or translation terminator sequences.

One of skill can produce a nucleic acid template that encodes a fusion protein using methods well known in the art. Basic texts disclosing general methods and techniques in the field of recombinant genetics include Green, M. R., and Sambrook, J., eds., Molecular Cloning: A Laboratory Manual, 4th ed., Cold Spring Harbor Laboratory Press, Cold Spring Harbor, N.Y. (2012), and Ausubel, F. M., et al., Current Protocols in Molecular Biology (Supplement 99), John Wiley & Sons, New York (2012), which are incorporated herein by reference. Examples of appropriate molecular techniques for generating recombinant nucleic acids are found in Berger and Kimmel, Guide to Molecular Cloning Techniques, Methods in Enzymology (Volume 152 Academic Press, Inc., San Diego, Calif. 1987); and Innis et al., PCR Protocols: A Guide to Methods and Applications (Academic Press, San Diego, Calif. 1990), which are incorporated by reference herein. Methods for primer design and optimization of PCR conditions are well known in the art and can be found in standard molecular biology texts such as Ausubel et al., Short Protocols in Molecular Biology, 5$^{th}$ Edition, Wiley, 2002, and Innis et al., supra. Computer programs are useful in the design of primers with the required specificity and optimal amplification properties (e.g., Oligo Version 5.0 (National Biosciences)). In some embodiments, the PCR primers may additionally contain recognition sites for restriction endonucleases, to facilitate insertion of the amplified DNA fragment into specific restriction enzyme sites in a vector. If restriction sites are to be added to the 5' end of the PCR primers, it is preferable to include extra 5' bases to allow more efficient cleavage by the enzyme. In some embodiments, the PCR primers may also contain an RNA polymerase promoter site, such as T7 or SP6, to allow for subsequent in vitro transcription. Methods for in vitro transcription are well known to those of skill in the art (see, e.g., Van Gelder et al., Proc. Natl. Acad. Sci. U.S.A. 87:1663-1667, 1990; Eberwine et al., Proc. Natl. Acad. Sci. U.S.A. 89:3010-3014, 1992).

The construction of nucleic acid templates that encode the fusion proteins described herein can also be accomplished using gene synthesis techniques. The use of gene synthesis techniques allows for the individual components of the fusion proteins to be assembled in various combinations. Nucleic acids produced by gene synthesis techniques can encode fusion proteins described herein.

The recombinant or synthesized polynucleotides that encode the fusion proteins described herein can be transfected into host cells in order to express the fusion proteins. Standard transfection methods are used to produce bacterial, mammalian, yeast, insect, or plant cell lines that express the recombinant fusion proteins of this invention, which are then purified using standard techniques (see, e.g., Colley et al., *J. Biol. Chem.* 264: 17619-17622 (1989); *Guide to Protein Purification, in Methods in Enzymology*, vol. 182 (Deutscher, ed., 1990); Coligan et al., Current Protocols in Protein Science, Vol. 1, John Wiley and Sons, Inc., New York (2000)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA, or other foreign genetic material into a host cell (see, e.g., Green and Sambrook, supra).

D. Detecting the Bound Affinity Agent

After the small analyte is bound to the antibody in an immune complex, the immune complex is contacted with the affinity agent under conditions suitable for binding of the peptides of the affinity agent to the immune complex. Conditions suitable for binding of the affinity agent to the immune complex are provided in the Examples. Detection of the bound affinity agent to the antibody-small analyte IC can be performed using any means known in the art. In some embodiments, the affinity agent is labeled and detection of the label detects the antibody-small analyte-affinity agent complex. In some embodiments, the self-associated oligomeric protein is conjugated to a detectable label. In some embodiments, a secondary detection molecule (e.g., an antibody) that specifically binds to the oligomeric protein of the affinity agent is contacted with the antibody-small analyte-affinity agent complex. Detection of the secondary detection molecule detects the antibody-small analyte-affinity agent complex, thereby detecting the small anlyte in the sample. In some embodiments, the secondary detection molecule is labeled with a detectable label.

The particular label or detectable group used in the assay is not a critical aspect of the invention, as long as it does not significantly interfere with the specific binding of the antibody to the small analyte. The detectable group can be any material having a detectable physical or chemical property. Thus, a label is any composition detectable by spectroscopic, photochemical, biochemical, electrical, optical or chemical means. A wide variety of labels may be used, with the choice of label depending on sensitivity required, ease of conjugation with the compound, stability requirements, available instrumentation, and disposal provisions. Useful labels in the present invention include magnetic beads (e.g., DYNABEADS™), fluorescent dyes (e.g., fluorescein isothiocyanate, Texas red, rhodamine, and the like), radiolabels (e.g., $^{3}$H, $^{125}$I, $^{35}$S, $^{14}$C, or $^{32}$P), and colorimetric labels such as colloidal gold or colored glass or plastic beads (e.g., polystyrene, polypropylene, latex, etc.). In some embodiments, the detectable label is an enzyme, a fluorescent label, a dye, or a magnetic particle. In some embodiments, the affinity agent is labeled with a dye, such as carbon black.

The molecules can be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, e.g., U.S. Pat. No. 4,391,904.

Means of detecting labels are well known to those of skill in the art. Thus, for example, where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10.degree. C. to 40.degree. C.

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. For example, protein compositions such as bovine serum albumin (BSA), nonfat powdered milk, and gelatin are widely used to reduce non-specific binding. The methods of the invention can be performed using an ELISA format, as described in the Examples.

IV. Devices

A major advantage of noncompetitive assays is that they can be developed into simple formats with a positive visual endpoint. Thus, the present disclosure provides devices for detecting small analytes that provide a positive visual readout. In some embodiments, the device comprises a capture antibody immobilized on a solid support, where the antibody is capable of specific binding to the small analyte of interest. The device also comprises an affinity agent described herein. Thus, in some embodiments, the device comprises a self-associated oligomeric protein displaying multiple copies of a peptide. Each peptide is capable of specifically binding to an immune complex formed when the antibody binds to the analyte. In some embodiments, the peptide is from about 5 to about 50 amino acids in length. In some embodiments, the analyte has a molecular weight of less than about 2500 daltons.

In order to detect binding of the affinity agent to the immune complex, the self-associated oligomeric protein of the device is conjugated to a detectable label. In some embodiments, the detectable label is detectable by the human eye. For example, the detectable label can be a dye, such as carbon black.

In other embodiments, rather than having the capture antibody immobilized on the solid support, the affinity agent is immobilized on a solid support. The affinity agent is capable of specifically binding to an immune complex formed when the antibody binds to the analyte. Thus, in these embodiments, the analyte is contacted with the antibody resulting in formation of an immune complex. The analyte can be contacted with the antibody in solution, or the antibody can be attached to a solid support, such as a bead or magnetic bead. The resulting immune complex is then contacted with the immobilized affinity agent. The bound immune complex is detected as described herein, for example, by directly labeling the antibody with a detectable label, or by using a labeled secondary antibody that binds to the first capture antibody.

A. Dipstick Devices

One attractive advantage of noncompetitive assays is the possibility of measuring near-zero signals at low analyte concentration. This is a key feature that explains the improved sensitivity of noncompetitive assays over competitive ones, but it is also an advantageous property that facilitates their adaptation into rapid test formats, particularly when the presence of the analyte needs to be visualized in a yes or no fashion. Thus, the assay was adapted into a dipstick format where the antibody was immobilized onto a solid support, such as nitrocellulose. In the dipstick format, different amounts of the capture antibody are spotted onto the solid support in discrete regions. For example, from about 1.0 µg/cm$^2$ to about 100 µg/cm$^2$ of antibody can be spotted onto non-overlapping regions of the solid support. To detect the analyte, the solid support is dipped into the analyte solution.

Figure 4:
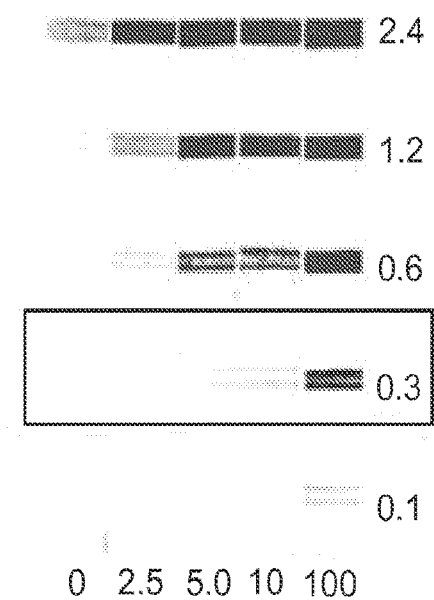
FIG. 4 shows the results of a noncompetitive dipstick assay for molinate. MoAb 14D7 was printed on nitrocellulose at different densities (ng/cm2) as indicated on the right hand side. Strips were cut and tested with SPO-pA and various concentrations of molinate (ng/ml/), as shown on the bottom. The peroxidase activity was developed with diaminobenzidine.

The formation of the IC is revealed by its reaction with the affinity agent. This reaction can be visualized either by direct labeling of the affinity agent or with the use of a secondary antibody. For example, the affinity agent can be labeled with an enzyme, such as horse radish peroxidase (HRP), that produces a colored reaction product upon addition of the appropriate substrate, as shown in FIG. 4 and described in the Examples. The affinity agent can also be labeled with a dye, such as carbon black, as described in the Examples.

B. Lateral Flow Devices

The nanopeptamers described herein are also useful in lateral flow immunochromatography devices for detecting small analytes. In lateral flow devices, the capture antibody is printed on a solid support such as a nitrocellulose membrane. The capture antibody can be printed at a density of about 1.0 µg/cm$^2$ to about 100 µg/cm$^2$. The affinity agent is labeled with a detectable label. In some embodiments, the detectable label is a dye, such as carbon black. However, any detectable dye or label can be used. The dye can be used in a colloidal suspension to label the affinity agent. Further, labels that are not visible to the unaided human eye can also be used, such as certain fluorescent dyes, as long as the label is detectable by a method known in the art, as described herein.

To detect the analyte in a lateral flow assay, the labeled affinity agent is added to a solution suspected of containing the target analyte, and the solid support comprising the capture antibody immobilized thereon is contacted with the solution under conditions sufficient for binding of the analyte to the capture antibody. The solid support is typically dipped into the solution such that the solution flows along the solid support, which results in a visible line on the solid support if the analyte is present. The lateral flow assays described herein are capable of detecting concentrations as low as 2.5 ng/ml of the herbicides molinate and clomazone. For comparison, a lateral flow competitive assay for molinate using the same capture antibody was able to detect a lower limit of 32 ng/ml, as described in the Examples. Thus, in addition to providing a positive readout, the noncompetitive lateral flow assay provided 10-fold improved sensitivity over a comparable competitive assay.

In another embodiment of a lateral flow device, multivalent expression of the peptide specific for the immune complex is directly obtained by attachment of the peptide to a solid support such as colored or dyed beads. Positive binding of the peptide-bead affinity agent to the analyte is detected by the presence of a visible line due to the colored beads.

In another embodiment of a lateral flow device, the affinity agent is immobilized on the solid support, and the solid support is contacted with a sample comprising the capture antibody and the analyte. The sample is incubated under conditions sufficient for binding of the analyte-antibody immune complex to the affinity agent to occur. Suitable conditions are provided in the Examples. Binding of the IC to the affinity agent is detected by directly labeling the capture antibody with a detectable label, or by a labeled secondary antibody that binds to the capture antibody.

The use of nanopeptamers in lateral flow assays offers advantages over the phage anti-immune complex assay (PHAIA) described in US 2008/0305559. For example, attempts to adapt PHAIA into lateral-flow assays were not successful, most probably due to the formation of aggregates between the phage particles and the colloidal dye labels. Thus, even though the phage particles express the same anti-immune complex peptides as the nanopeptamers described herein, nanopeptamers provide improvements over phage particles in the development of positive readout assays for detecting small analytes.

The lateral flow assays described herein were also tested for matrix interference effects. For example, known concentrations of molinate are spiked into runoff water samples from agricultural areas, and the samples analyzed by the lateral flow device. As described in the Examples, concentrations as low as 2.5 ng/ml of molinate were detectable in all the samples, indicating that the sensitivity of the assay was not affected by the source of the sample.

V. Examples

The embodiments of the present invention are further illustrated by the following examples. These examples are offered to illustrate, but not to limit the claimed invention.

Example 1

Detection of Small Analytes Using Nanopeptamers in a Noncompetitive Assay

This example demonstrates that nanopeptamers can detect small analytes in a noncompetitive immunoassay.

In this example, a nanopeptamer comprising streptavidin was used to develop noncompetitive assays for the analytes molinate and clomazone. Peptides that specifically bind molinate and clomazone were conjugated to biotin, resulting in high affinity binding of the biotinylated peptides to streptavidin. The streptavidin-biotinylated peptide complexes are referred to as nanopeptamers.

A. Materials and Methods

Molinate and the thiocarbamate compound standards used in the immunoassays were gifts from Stauffer Chemical Co. Thiobencarb was a gift from Chevron Chemical Co. Development of the monoclonal anti-molinate antibody (MoAb 14D7) and anti-clomazone antibody (MoAb 5.6) has been described in detail previously (Carlomagno, M.; Matho, C.; Cantou, G.; Sanborn, J. R.; Last, J. A.; Hammock, B. D.; Roel, A.; Gonzalez, D.; Gonzalez-Sapienza, G. J Agric Food Chem 2010, 58, 4367; Rufo, C.; Hammock, B. D.; Gee, S. J.; Last, J. A.; Gonzalez-Sapienza, G. J Agric Food Chem 2004, 52, 182). Clomazone was purchased from Riedel-de Haen (Seelze, Germany). High-sensitivity Streptavidin-Peroxidase (SPO) was purchased from Pierce (Rockford, Ill.). Bovine Serum Albumin (BSA), TWEEN 20, and 3,3',5,5'-tetramethylbenzidine (TMB) and avidin were obtained from Sigma (St. Louis, Mo.). High and low binding ELISA and dilution microtiter polystyrene plates, were purchased from Greiner (Solingen, Germany). Hi-Flow Plus 120 nitrocellulose membrane cards and cellulose absorbent pads were purchased from Millipore (Bedford, Mass.). Carbon black nanoparticles were purchased from Degussa AG (Frankfurt, Germany).

1. Production of Nanopeptameres that Bind Anti-Molinate and Anti-Clomazone Immunocomplexes Two peptidic sequences previously isolated yielding highly sensitive non-competitive immunoassays for molinate (Gonzalez-Techera, A.; Vanrell, L.; Last, J. A.; Hammock, B. D.; Gonzalez-Sapienza, G. Anal Chem 2007, 79, 7799), and one peptidic sequence recognizing clomazone (Rossotti, M. A.; Carlomagno, M.; Gonzalez-Techera, A.; Hammock, B. D.; Last, J.; Gonzalez-Sapienza, G. Anal Chem 2010) when bore on the phage particle were produced by a commercial manufacturer (Peptron Co., Daejeon, Korea). These peptides were produced at 5 mg scale, at an eighty percent of purity by HPLC, with intramolecular disulfides bonds between cysteines, with a biotin molecule in its N terminus and amidated C-terminus. The synthesized peptides sequences for molinate are: Biotin-SGSGCSLWDTTGWC (peptide A: SEQ ID NO:1) and Biotin-SGSGCSTWDTTGWC (peptide 1M: SEQ ID NO:2) (peptidic sequence is shown in black and a spacer between the peptide and the biotin molecule is underlined). The synthesized peptide sequence for clomazone anti-IC is Biotin-SGSGCLEAPNIEGC (peptide ICX11: SEQ ID NO:3).

Taking into account that each Streptavidin molecule binds four biotin molecules, biotinylated anti-molinate and anti-clomazone IC peptides were incubated with SPO to form Nanopeptamers (6.25-fold molar excess of biotinylated peptide). In particular, 24 µg of SPO (i.e: approximately 0.24 nanomoles, if all of the SPO was streptavidin) were incubated with 6 nanomoles of biotinylated anti-molinate IC peptides in a final volume of 100 µl of 1% BSA in 1× phosphate-buffered saline (PBS). After incubation for 15 minutes in ice, appropriate dilutions of the Nanopeptamers were done for performing the assays described below.

2. Nanopeptamer Checkerboard Titrations

Microtiter plates were coated with 100 µl of anti-molinate monoclonal antibody (MoAb 14D7) in PBS at different concentrations. Rows A and B of the microtiter plate were coated with 10 µg/ml of 14D7 MoAb, rows C and D with 5 µg/ml, rows E and F with 2.5 µg/ml and rows G and H with 1.25 µg/ml in PBS.

After incubation for 1 hour at 37° C. and blocking 1 hour at 37° C. with BSA 1% in PBS, the microtiter plates were washed three times with PBS 0.05% TWEEN 20 (PBST). Serial 2-fold dilutions of SPO-peptides complexes (starting from a /1;10dilution) were performed in PBST in non-treated polystyrene plates (low binding capacity) in the presence (100 ng/mL) of molinate or in its absence. The Nanopeptamer dilutions were then transferred to wells precoated with 14D7 MoAb. After incubation for 1 h at room temperature, the plates were thoroughly washed. The peroxidase activity was then developed by adding 100µL of peroxidase substrate (25mL of 0.1 M citrate acetate buffer pH 5.5, 0.4 mL of 6 mg/mL DMSO solution of 3,3',5,5'-tetramethylbenzidine, and 0.1mL of 1% $H_2O_2$). The same procedure was performed with anti-clomazone Nanopeptamer.

3. Effect of the Final Concentration of Nanopeptamer in Assay Performance

Microtiter plates were coated with 10 µg/ml of 14D7 MoAb as described previously. Two-fold serial dilutions of standard molinate was mixed with nanopeptamer complex and used in ELISA at the following final nanopeptamer concentrations: 6, 3, 1.5, 0.75, 0.38 and 0.18 µg/ml. These dilutions were performed in low binding plates and then transferred to the coated and blocked wells of an ELISA plate. After incubating for 1 hour at room temperature and washing, the plates were revealed as described above.

4. Evaluation of SPO Saturation with Anti-Immunecomplex Peptides and Assay Sensitivity SPO was incubated with different amounts of biotinylated peptides. For this, 24 µg of SPO (i.e: approximately 0.24 nanomoles) were incubated with 48, 6.25, 1.5 and 0.58 nanomoles of biotinylated anti-molinate IC peptides in a final volume of 100 µl of 1% BSA in PBS. This represents a molar excess of 50, 6.5, 1.5, and 0.6 of biotinylated peptides A and 1M, respectively. After incubation for 1 hour in ice, a ¹/₁₆₀ dilution of each of these complexes were used for performing standard molinate curves.

5. Molinate Nanopeptamers Assay Cross-Reactivity

The specificity of the noncompetitive assays setup with pA-Nanopeptamer and p1M-Nanopeptamer was characterized by determining the cross-reactivity with related S-thiocarbamate pesticides. Analyte concentrations in the 0-10000 ng/mL range were used in the noncompetitive ELISAs. After the data was normalized, the molar compound concentration corresponding to the midpoint of the curve, which corresponds to the concentration of analyte producing 50% saturation of the signal ($SC_{50}$), was used to express the cross-reactivity of the assay according to the equation: % cross-reactivity=100×[$SC_{50}$(analyte)/$SC_{50}$(cross-reacting compound)].

6. Matrix Effect Analysis in ELISAs

For the analysis of matrix effects, runoff water samples from rural areas of Uruguay, with no register of use of molinate, were spiked with known amounts of analyte and assayed in the 0-100 ng/mL range, using 95 μL of undiluted water samples plus 5 μL of 10×PBST.

B. Results

As shown in FIG. 2, nanopeptamers comprising two peptides, pA and p1M, were used to develop noncompetitive assays for molinate. The dose response curves had a typical sigmoid shape with signal saturation at high concentration of molinate. The midpoint corresponding to the concentration of analyte giving 50% of signal saturation ($SC_{50}$) were 8.3±0.2 and 10.0±0.3 ng/mL for the pA and p1M-Nanopeptamers, respectively. The limit of detection (LOD=analyte concentration giving a 10% increase over the zero signal) were 1.2 and 3.2 ng/mL for pA and p1M-Nanopeptamers, respectively. The LOD attained with the nanopeptamers were up to 18-fold better than that of the competitive ELISA set up with the same antibody (LOD 22 ng/mL, IC50 69±0.5 ng/mL; see Rufo, C.; Hammock, B. D.; Gee, S. J.; Last, J. A.; Gonzalez-Sapienza, G. *J Agric Food Chem* 2004, 52, 182.).

The pA-Nanopeptamer was then used to characterize the cross-reactivity (specificity) of the affinity agent to other agrochemicals and pesticides. Cross-reactivity was tested using a panel composed of common agrochemicals utilized in rice culture (quinclorac, glyphosate, molinate, bispiribac, propanil, and atrazine.), as well as other S-thiocarbamate pesticides. As shown in Table 1, only minor cross-reactivity with closely related thiocarbamate compounds was observed, which was similar to that obtained with the PHAIA assay. The pA-Nanopeptamer was also used to characterize potential matrix effects that may decrease sensitivity of the assay. No matrix effect was observed when standard molinate curves were performed with undiluted agricultural run off-water samples from different areas of Uruguay (data not shown).

TABLE 1

Cross reactivity (%) of the pA-Nanopeptamer and PHAIA assays with related thiocarbamate pesticies.

| Compound | Structure | pA-Nanopeptamer | PHAIA |
|---|---|---|---|
| Molinate | 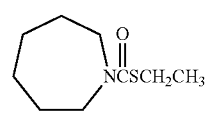 | 100 | 100 |
| thiobencarb | 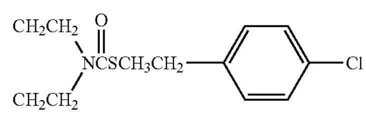 | 0 | 0 |
| Butylate | 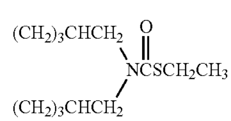 | 1 | 0 |
| EPTC | 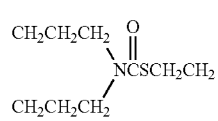 | 2 | 5 |
| Cycloate | 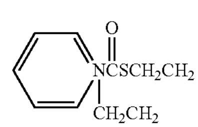 | 10 | 9 |
| Pebulate | 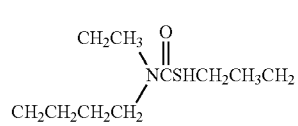 | 6 | 7 |

TABLE 1-continued

Cross reactivity (%) of the pA-Nanopeptamer and PHAIA
assays with related thiocarbamate pesticies.

| Compound | Structure | pA-Nanopeptamer | PHAIA |
|---|---|---|---|
| Vernolate | $CH_3CH_2CH_2$\\NCSCH$_3$CH$_2$CH$_3$ (O double bond)/$CH_3CH_2CH_2$ | 5 | 4 |

All data are the mean of two independent experiments. A value of 6 means that there was no observable cross reactivity with the highest concentration tested $10^2$ ng/ml To explore the general utility of the method, a nanopeptamer-based assay for the herbicide clomazone was developed. The anti-clomazone MoAb 5.6 was used as the capture antibody, and the anti-IC synthetic peptide pICX11 (biotin-SGSGCLEAPNIEGC; SEQ ID NO:3) complexed with SPO or avidin was used as the affinity agent. The pICX11 peptide was previously isolated from phage libraries panned against the clomazone-MoAb 5.6 IC (see, Carlomagno, M.; Matho, C.; Cantou, G.; Sanborn, J. R.; Last, J. A.; Hammock, B. D.; Roel, A.; Gonzalez, D.; Gonzalez-Sapienza, G. *J Agric Food Chem* 2010, 58, 4367.). For ELISA, the assay conditions were optimized essentially as described above for the molinate assay. As shown in FIG. 3, nanopeptamers comprising SPO and the peptide pX11 were capable of detecting clomazone in a noncompetitive assay, with a LOD=1.2 ng/mL and $SC_{50}$=3.4±0.2 ng/mL). This represents an improvement of 3.3 and 8.3-fold regarding the assay set up with the same antibody in a competitive format (LOD=4 ng/ml and IC50=28±1.1 ng/mL, respectively; see Carlomagno, M.; Matho, C.; Cantou, G.; Sanborn, J. R.; Last, J. A.; Hammock, B. D.; Roel, A.; Gonzalez, D.; Gonzalez-Sapienza, G. *J Agric Food Chem* 2010, 58, 4367).

The above example demonstrates that the affinity agents (e.g., nanopeptamers) of the invention are capable of detecting small analytes in noncompetitive assays with high specificity and high sensitivity.

Example 2

Devices for Detecting Small Analytes

This example demonstrates that the methods of the invention can be performed using an easy to read device, and that the device can detect small analytes at lower concentrations than a device used to perform a competitive assay directed to the same target analyte.

A. Dip Stick Devices

MoAb 14D7 was printed on nitrocellulose at different densities (0.1, 0.3, 0.6, 1.2, and 2.4 ng/cm$^2$). The nitrocellulose was cut into strips and contacted with SPO-pA and various concentrations of molinate (0, 2.5, 5.0, 10.0, and 100 ng/ml). The peroxidase activity was developed with diaminobenzidine.

As shown in FIG. 4, the pA-SPO nanopeptamer was capable of detecting immune complexes comprising molinate in a dipstick assay device. At high antibody coating densities of antibody MoAb 14D7, the residual cross-reactivity of the nanopeptamer with the unliganded antibody produced a visible signal. However, at lower coating densities, the background rapidly declines, and at a coating density of 0.3 ng/cm$^2$ a molinate concentration as low as 2.5 ng/ml was detectable by simple visual inspection of the strips. Such a small change in band intensity would be difficult to visualize in a competitive format, as it would represent only a small drop from the saturation signal. Thus, nanopeptamers offer distinct advantages in the development of point-of-care tests having visual end-point readouts.

B. Lateral Flow Devices

MoAb 14D7 and MoAb 5.6 lines were printed on Hi-Flow Plus 120 nitrocellulose membrane cards at 0.92 μg/cm using a BioDot AD 1500 Liquid Dispenser. Avidin was labeled with carbon black nanoparticles as described in the protocol below. Approximately 38 μg (100 μL) of carbon black-labeled avidin was preincubated with 15 μg of pA and 15 μg of pX11 (6 μL), respectively, in a final volume of 1×PBS containing 0.025% Tween-20. After incubation for 15 min on ice 2.5 μL of carbon black labeled Nanopeptamers were transferred to microtiter plates wells containing 100 μL of 1×PBS, 0.025% Tween previously spiked with known amounts of molinate and clomazone standards. Hi-Flow Plus 120 nitrocellulose membrane cards (printed with MoAbs 14D7 and 5.6) assembled with an absorbent cellulose pad were dipped into the wells and incubated for 10 minutes. After that, strips were read with naked eye by four independent observers in three different repetitions of the tests.

Molinate assays were validated by performing spiking in run off water samples of agricultural areas of Uruguay (95μL water sample+5μL PBS ×10, 0.025% TWEEN 20), and measuring them with strips as described above.

Carbon Black Nanopeptamers Labeling Protocol:
1) Dialyze avidin against 5 mM Boric Buffer pH=8.8
2) Put 1 mL of a 5% carbon black solution prepared in MilliQ water in a 1.5 mL eppendorf. Sonicate 1 min and pause 1 min. Repeat this step 3 times.
3) Dilute the 5% suspension to 0.2% in 5 mM boric Buffer pH=8.8. Repeat sonication as described above.
4) Mix 380 μg of avidin (20-200 μ) with 0.2% carbon black in 5 mM boric Buffer pH=8.8 in a final volume of 1 mL. Repeat sonication as described above.
5) Incubate at least 3 hours at room temperature or overnight at 4° C.
6) Centrifugate at 14.000 rpm for 15 minutes.
7) Resuspend in 1 mL of Running Buffer (RB: 100 mM Boric Buffer pH=8.8, 0.02% TWEEN 20). This will block free binding sites of carbon black. Repeat sonication. Incubate at room temperature for 10 minutes. Centrifuge, discard supernatant. Repeat these step 7, 3 times.
8) Finally, resuspend in 1 mL of Boric Buffer.

Figure 5:
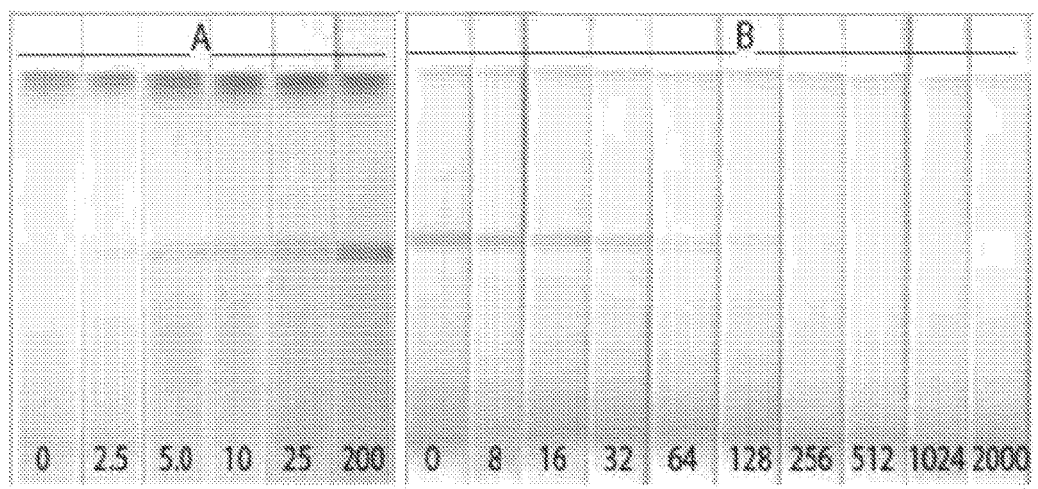
FIG. 5 shows the results of a noncompetitive nanopeptamer pA-based (A) and competitive (B) lateral-flow assays for molinate. The nitrocellulose strips were tested with buffer containing various concentrations of molinate (ng/mL), as denoted in the figure. A molinate concentration of 2.5 ng/mL caused a visible test line over the background in the noncompetitive assay, while 32 ng/ml produced a weaker test line than the negative control in the competitive assay, as was agreed upon by four independent observers in three different repetitions of the test.

As shown in FIG. 5, the pA-nanopeptamer was capable of detecting immune complexes comprising molinate in a lateral flow assay device. FIG. 5A shows the results of a lateral-flow-assay using MoAb 14D7 as capture reagent immobilized on polyester-backed nitrocellulose membranes and colloidal-carbon labelled avidin complexed to pA for detection. For the sake of comparison, a competitive assay for molinate was also developed in a lateral-flow format using MoAb 14D7 as capture antibody and the molinate derivative 7b (S-2-(p-aminophenyl)-ethyl-hexahydroazepine-1-carbothioate) coupled to conalbumin, which was labelled with colloidal carbon for detection (see FIG. 5B). A molinate concentration of 2.5 ng/mL caused a visible test line in the noncompetitive assay, while 32 ng/mL produce a weaker test line than the negative control in the competitive assay; as was agreed upon by four independent observers in three different repetitions of the test. Thus, in addition to providing a positive reading that is easy to interpret, the noncompetitive test also performed with a 10-fold improved sensitivity. The assay was then tested for matrix interference using ten runoff water samples from agricultural areas of Uruguay spiked with 0, 2.5, 5, and 20 ng/mL of molinate. The strips were read by four independent observers, all of whom detected a visible reaction line for all samples except the zero-spiked control, indicating that the source of the sample did not interfere with assay sensitivity.

Figure 6:
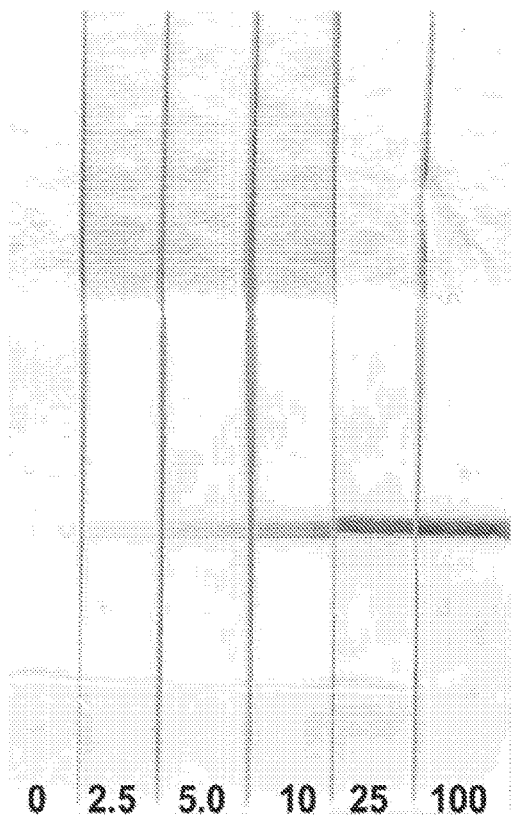
FIG. 6 shows the results of a noncompetitive nanopeptamer lateral flow assay for clomazone. Nitrocellulose strips were tested with buffer containing various concentrations of clomazone (ng/mL) as denoted in the lower part of the figure. The clomazone concentration of 2.5 ng/mL caused a visible test line over the background in the noncompetitive assay as was agreed upon by four independent observers in three different repetitions of the test.

As shown in FIG. 6, a lateral flow assay capable of detecting clomazone was also developed using a nanopeptamer comprising avidin and the peptide pX11. The lateral flow assay was capable of detecting a clomazone concentration as low as 2.5 ng/ml, indicated by the visible test line over background, as was agreed upon by four independent observers in three different repetitions of the test.

This example demonstrates that noncompetitive immunoassays that use the affinity agents of the invention can be adapted to devices that perform with increased sensitivity compared to devices using competitive immunoassays, and that the target analyte can be detected in a direct, positive-readout, user-friendly device.

Example 3

Recombinant Nanopeptamers

This example demonstrates that nanopeptamers comprising recombinant fusion proteins can detect the small analytes molinate and clomazone in noncompetitive immunoassays.

The embodiment described in the above example makes use of nanopeptamers having biotinylated peptides that bind streptavidin and/or avidin. In this example, nanopeptamers were constructed using recombinant fusion proteins that comprise an oligomeric core protein and peptides that specifically bind the target analyte. The use of fusion proteins simplifies the assay and avoids the cost of synthesizing biotinylated peptides. This example describes two different recombinant nanopeptamer platforms, a streptavidin-peptide and a verotoxin-peptide recombinant nanopeptamer.

A. Streptavidin-Peptide Recombinant Nanopeptamers

In this example, the monomeric subunit of core streptavidin is produced in *E. coli* as a recombinant chimeric protein with the anti-immunocomplex peptide fused to its N-, C-, or N- and C-terminus. After spontaneous tetramerization, these streptavidin Nanopeptamers display 4 or 8 copies of the anti-immunocomplex peptides leaving the biotin binding sites available for versatile combination with available biotinylated conjugates, such as biotin-enzyme, biotin-fluorescent compounds, biotin-dyes, etc (FIG. 7a). This example describes the development of recombinant Nanopeptamers for the detection of the herbicides clomazone and molinate.

The gene coding for *Streptomyces avidinii* streptavidin (amino acids 14-159, accession code CAA00084.1) was optimized for expression in *E. coli* and synthesized by IDT (Integrated DNA Technologies). The streptavidin gene was then amplified by PCR using the streptavidin template and employing the primers shown in Box 1. The forward primers encoded the sequences of peptides pICX11 and pA, previously isolated for the specific recognition of the immunocomplexes (ICs) MoAb5.6-clomazone (Rossotti, M. A., et al., *Phage Anti-Immunocomplex Assay for Clomazone: Two-Site Recognition Increasing Assay Specificity and Facilitating Adaptation into an On-Site Format*. Anal Chem, 2010), and MoAb14D7-molinate (Gonzalez-Techera, A., et al., *Phage anti-immune complex assay: general strategy for noncompetitive immunodetection of small molecules*. Anal Chem, 2007. 79(20): p. 7799-806), respectively, and thus the amplified cassette included the coding sequence of the peptides fused through a spacer to the coding sequence of core streptavidin, flanked by two non-complementary SfiI sites.

```
Box 1: Primers for streptavidin-peptide chimeras constructions (SEQ ID
NOS: 8-16)
PRIMER A (5'-3') FORWARD SfiI (1)    G₂ SPACER              ICX11 PEPTIDE
A AAA AAG GCC CAG GCG GCC GGA GGC TGT CTG GAG GCG CCG AAC ATT GAA GGC TGC
        K   K   A   Q   A   A   G   G   C   L   E   A   P   N   I   E   G   C (G₃S)₂ SPACER                 STREPTAVIDIN
GGT GGC GGC TCT GGA GGT GGC AGT GCC GCC GAA GCC GGC ATC ACG
 G   G   G   S   G   G   G   S   A   A   E   A   G   I   T Primer B (5'-3') FORWARD SfiI (1)      ASGSA SPACER          pA PEPTIDE
T TTA AAG GCC CAG GCG GCC GCA TCC GGC AGC GCC TGC TCC CTG TGG GAC ACC ACA
        L   K   A   Q   A   A   A   S   G   S   A   C   S   L   W   D   T   T GP₆G SPACER                  STREPTAVIDIN
GGC TGG TGT GGC CCT CCT CCT CCT CCT CCT GGC GCC GCC GAA GCC GGC ATC ACG GGC
 G   W   C   G   P   P   P   P   P   P   G   A   A   E   A   G   I   T   G
```

```
PRIMER C (5'-3') REVERSE
         STREPTAVIDIN                 SfiI (2)
      GTT AAA CCG TCT GCC GCG TCC GGC CAG GCC GGC CTT TTT T-3'
       V   K   P   S   A   S   G   Q   A   G   L   F
```

The SfiI sites were used to clone the cassette into the expression vector pet-OmpA. The important features of this vector (constructed in our laboratory by modification of the pet28a vector (Novagen, Madison, Wis.)) are shown in box 2. Briefly, the vector encodes a peptidic signal sequence (OmpA) which directs the synthesized protein to the periplasmic space of *E. coli*, two SfiI non-complementary sites allows directional cloning of the gene of interest, between the OmpA sequence and nucleotide sequence of a histidine tail (His6; SEQ ID NO:17), the HA epitope, and STOP codons. The construct expression is under the control of the bacteriophage T7 promoter, and is induced when T7 RNA polymerase is synthesized by the host cell *E. coli* BL21 (DE3) after addition of IPTG.

B. Verotoxin-Peptide Recombinant Nanopeptamers.

Another example of a multimeric protein that can be used as a nanopeptamer core protein is the verotoxin 1 B-subunit (or shiga-like toxin 1) produced by *E. coli* O157:H7. Verotoxin 1 is the smallest of the family of $AB_5$ toxins in which the A subunit is the toxic entity and the pentameric B-subunit mediates binding to host cell surfaces. The 7.7 kDa VT1B subunit monomers self-assemble to form a 38.5 kDa homopentamer that is fully functional in terms of host cell binding in the absence of the A subunit. This section describes the production of recombinant verotoxin nanopeptamers that are capable of detecting molinate and atrazine with high sensitivity in noncompetitive immunoassays.

```
Box 2: Important features of pET-OmpA (SEQ ID NOS: 17-19)
 -------------------- OmpA Signal Sequence ------------    SfiI (1)
 ATGAAAAAGACAGCTATCGCGATTGCAGTGGCACTGGCTGGTTTCGCTACCGT G GCC CAG GCG SfiI (2)                 His6-Tag
 GCC GENE OF INTEREST GGC CAG GCC GGC CAG CAC CAT CAC CAT CAC CAC GGC GCA TAC CCG TAC GAC GTT CCG GAC TAC GCT AGC  GATCC TAG TAG CTCGAG
        ------------- HA epitope ----------- BamHI    2Stop  XhoI
```

After streptavidin-peptide expression induction with IPTG chimeric proteins were only found in the insoluble fraction of the bacterial extract as inclusion bodies (FIG. 7*b*). For both chimeras the best buffer for solubilization and denaturation was Tris-urea 8M, pH=11. Streptavidin-pA refolding was performed by slow dilution in buffer 50 mM Tris, 30% glycerol, pH=9. For streptavidin-ICX11 the best refolding buffer was 0.1M Tris, 1.5 M sucrose, pH 7. Both chimeras were purified by affinity chromatography using affinity $Ni^{2+}$/EDTA HisTrap HP columns. In both cases the final yield of purified protein was 3-6 mg/L of bacterial culture.

For the detection of immunocomplexes by ELISA, the same coating concentrations described in Example 1 were used, and 100 μl of 5 μg/mL of chimeric protein (diluted in PBS-0.05% Tween) was added in the presence of increasing molinate or clomazone concentrations. Finally, plates were revealed by the addition of HRP-biotin and its substrate. FIG. 7 (c and d) shows that the ELISA sensitivity using these nanopeptamers was similar to that obtained with the PHAIA format for both pesticides (Rossotti, M. A., et al., and Gonzalez-Techera, A., et al., supra), showing that recombinant Nanopeptamers are a salient option for the development of phage-free highly sensitive noncompetitive assays for small analytes.

The gene for the verotoxin-pA chimera, encoding peptide pA (specific for the molinate IC described above) at the N-terminus of the verotoxin 1 B subunit (nt: 1349-1555, EMBL M16625, SEQ ID NO:20) was synthetized by IDT (Integrated DNA Technologies, Coralville, Iowa) as a cassette flanked by two non-complementary SfiI sites as detailed in (Box 3). This plasmid was digested with SfiI and cloned into the vector pET-OmpA to obtain the pET-OmpA-VXTpA vector. This vector was used for expression of the verotoxin-pA chimera as described above.

The verotoxin 1 B subunit was also used to construct a fusion protein with the A9 peptide, which is specific for the immunocomplex formed by the herbicide atrazine with its subrogate antibody MoAbK4E7 (Gonzalez-Techera, A., et al., *Phage anti-immune complex assay: general strategy for noncompetitive immunodetection of small molecules*. Anal Chem, 2007. 79 (20): p. 7799-806; Giersch, T., *A new monoclonal antibody for the sensitive detection of atrazine with immunoassay in microtiter plate and dipstick format*. J. Agric. Food Chem., 1993. 41 (6): p. 1006-1011). This chimera consists of peptide pA9 which is fused through a spacer to the N-terminus of the verotoxin subunit (Box 3). To this end, primers D and E were annealed, inserted into the plasmid pET-OmpA-VXTpA previously digested with the KpnI and PstI enzymes, and ligated to build the plasmid pET-OmpA-VXTpA9, which was used for expression of the chimeric protein as described above.

```
Box 3:

Verotoxin-pA chimera construction (SEQ ID NOS: 13, 21, 22 and 10)

SfiI (1)        KpnI      ASGA spacer           pA peptide
 G GCC CAG GCG GCC GGT ACC GCA TCC GGC AGC GCC TGC TCC CTG TGG GAC ACC
    A   Q   A   A   G   T   A   S   G   S   A   C   S   L   W   D   T
```

```
                        PstI           (G3S)2 SPACER
               ACA GGC TGG TGT CTG CAG GGT GGC GGC TCT GGA GGT GGC AGT ACG CCT GAT
                T   G   W   C   L   Q   G   G   G   S   G   G   S   T   P   D

VEROTOXIN 1 B-SUBUNIT
               TGT GTA ACT GGA AAG GTG GAG TAT ACA AAA TAT AAT GAT GAC GAT ACC TTT
                C   V   T   G   K   V   E   Y   T   K   Y   N   D   D   D   T   F

ACA GTT AAA GTG GGT GAT AAA GAA TTA TTT ACC AAC AGA TGG AAT CTT CAG
                T   V   K   V   G   D   K   E   L   F   T   N   R   W   N   L   Q

TCT CTT CTT CTC AGT GCG CAA ATT ACG GGG ATG ACT GTA ACC ATT AAA ACT
                S   L   L   L   S   A   Q   I   T   G   M   T   V   T   I   K   T

SfiI (2)
               AAT GCC TGT CAT AAT GGA GGG GGA TTC AGC GAA GTT ATT TTT CGT GGC CAC
                N   A   C   H   N   G   G   G   F   S   E   V   I   F   R   G   Q

GCC GGC C
                A   G

Primers for verotoxin-A9 chimera construction
Primer D (SEQ ID NO: 23)
     KpnI overhang SfiI (1)      A9 peptide sequence           PstI overhang
  5' C GGATCCGGCAGCGGC Tgt ccg tcg tcg agg tgg ttt gat ttg tgt ctg ca 3'

Primer E (SEQ ID NO: 24)
     KpnI overhang SfiI (2)     A9 complementary sequence     PstI overhang
  3' CATGG CGTAGCCGTCCGCCG Aca ggc agc agc tcc acc aaa cta aac aca G 5'
```

1. Protein Expression

In this case, a substantial fraction of the verotoxin-peptide chimeric proteins were found in the soluble fraction of the bacterial extract (FIG. 8b). After cell lysing by osmotic shock, the recombinant proteins were purified by affinity chromatography using $Ni^{2+}$/EDTA HisTrap HP columns. The final yield of purified proteins was about 20 mg/L of bacterial culture. Finally, the verotoxin-peptide Nanopeptamers were conjugated to HRP by reductive amination after activation of HRP with periodate, and these Nanopeptamer-HRP conjugates were used to perform the ELISA assays (FIG. 8a). Plates were coated with MoAb14D7 (10 μg/mL) or MoAbK4E7 (5 μg/mL) (Giersch, T., supra), the recombinant verotoxin-peptide chimera was added (5 μg/mL) in the presence of increasing amounts of analyte, and the plates were revealed with the HRP substrate. The use of Nanopeptamers-HPR conjugates allowed shortening the assay (one less step) as compared to the streptavidin-peptide ELISA format, while maintaining similar sensitivity values as the PHAIA format (FIG. 8c, 8d and Gonzalez-Techera, A., et al., supra).

This example demonstrates that recombinant nanopeptamers are capable of detecting small analytes with high sensitivity in ELISA assays, and that two different self-associating oligomeric proteins, streptavidin and verotoxin 1 B subunit, can be used as fusion partners for IC-specific peptides.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

Sequences:

Immune complex specific peptides

| Immune complex | name | Sequence (SEQ ID NO:) | Reference |
|---|---|---|---|
| molinate-MAb 14D7 | p1M | CSTWDTTGWC (5) | Gonzalez-Techera et al., Anal Chem 79: 7799-806 (2007) |
| molinate-MAb 14D7 | pA | CSLWDTTGWC (4) | Gonzalez-Techera et al., Anal Chem 79: 7799-806 (2007) |
| clomazone-Mab 5.6 | pICX11 | CLEAPNIEGC (6) | Rossotti et al., Anal Chem 21: 8838-8843 (2010) |
| atrazine-MAb K4E7 | pA9 | CPSSRWFDLC (7) | Gonzalez-Techera et al., Anal Chem 79: 7799-806 (2007) |

| Biotinylated peptides used for nanopeptamer construction | |
|---|---|
| name | Sequence (SEQ ID NO:) |
| p1M | biotin-SGSGCSTWDTTGWC (2) |
| pA | biotin-SGSGCSLWDTTGWC (1) |
| pICX11 | biotin-SGSGCLEAPNIEGC (3) |

Recombinant nanopeptamer subunits (protein subunit sequence is underlined)

Streptavidin-pA
(SEQ ID NOS: 25 and 26)
```
GCA TCC GGC AGC GCC TGC TCC CTG TGG GAC ACC ACA GGC TGG TGT GGC CCT CCT CCT CCT CCT CCT
 A   S   G   S   A   C   S   L   W   D   T   T   G   W   C   G   P   P   P   P   P   P
GGC GCC GCC GAA GCC GGC ATC ACG GGC ACT TGG TAC AAC CAG CTG GGT AGC ACC TTT ATT GTC ACC
 G   A   A   E   A   G   I   T   G   T   W   Y   N   Q   L   G   S   T   F   I   V   T
GCG GGC GCC GAT GGG GCA CTG ACA GGT ACC TAT GAG AGC GCT GTG GGC AAC GCA GAG AGC CGC TAT
 A   G   A   D   G   A   L   T   G   T   Y   E   S   A   V   G   N   A   E   S   R   Y
GTG CTG ACC GGG CGC TAT GAT TCC GCC CCG GCC ACC GAT GGT TCT GGT ACG GCC CTG GGT TGG ACG
 V   L   T   G   R   Y   D   S   A   P   A   T   D   G   S   G   T   A   L   G   W   T
GTG GCT TGG AAG AAT AAC TAT CGT AAC GCG CAT TCC GCC ACT ACC TGG TCC GGT CAA TAT GTG GGC
 V   A   W   K   N   N   Y   R   N   A   H   S   A   T   T   W   S   G   Q   Y   V   G
GGG GCC GAA GCA CGT ATT AAT ACC CAG TGG CTG TTA ACC TCT GGT ACG ACC GAA GCC AAC GCC TGG
 G   A   E   A   R   I   N   T   Q   W   L   L   T   S   G   T   T   E   A   N   A   W
AAG AGC ACC CTG GTC GGC CAT GAT ACG TTT ACC AAA GTT AAA CCG TCT GCC GCG TCC GGC CAG GCC
 K   S   T   L   V   G   H   D   T   F   T   K   V   K   P   S   A   A   S   G   Q   A
GGC CAG CAC CAT CAC CAT CAC CAC GGC GCA TAC CCG TAC GAC GTT CCG GAC TAC GCT AGC GGA TCC
 G   Q   H   H   H   H   H   H   G   A   Y   P   Y   D   V   P   D   Y   A   S   G   S
TAG TAG
```

Streptavidin-pICX11
(SEQ ID NOS: 27 and 28)
```
GGA GGC TGT CTG GAG GCG CCG AAC ATT GAA GGC TGC GGT GGC GGC TCT GGA GGT GGC AGT GCC GCC
 G   G   C   L   E   A   P   N   I   E   G   C   G   G   G   S   G   G   G   S   A   A
GAA GCC GGC ATC ACG GGC ACT TGG TAC AAC CAG CTG GGT AGC ACC TTT ATT GTC ACC GCG GGC GCC
 E   A   G   I   T   G   T   W   Y   N   Q   L   G   S   T   F   I   V   T   A   G   A
GAT GGG GCA CTG ACA GGT ACC TAT GAG AGC GCT GTG GGC AAC GCA GAG AGC CGC TAT GTG CTG ACC
 D   G   A   L   T   G   T   Y   E   S   A   V   G   N   A   E   S   R   Y   V   L   T
GGG CGC TAT GAT TCC GCC CCG GCC ACC GAT GGT TCT GGT ACG GCC CTG GGT TGG ACG GTG GCT TGG
 G   R   Y   D   S   A   P   A   T   D   G   S   G   T   A   L   G   W   T   V   A   W
AAG AAT AAC TAT CGT AAC GCG CAT TCC GCC ACT ACC TGG TCC GGT CAA TAT GTG GGC GGG GCC GAA
 K   N   N   Y   R   N   A   H   S   A   T   T   W   S   G   Q   Y   V   G   G   A   E
GCA CGT ATT AAT ACC CAG TGG CTG TTA ACC TCT GGT ACG ACC GAA GCC AAC GCC TGG AAG AGC ACC
 A   R   I   N   T   Q   W   L   L   T   S   G   T   T   E   A   N   A   W   K   S   T
CTG GTC GGC CAT GAT ACG TTT ACC AAA GTT AAA CCG TCT GCC GCG TCC GGC CAG GCC GGC CAG CAC
 L   V   G   H   D   T   F   T   K   V   K   P   S   A   A   S   G   Q   A   G   Q   H
CAT CAC CAT CAC CAC GGC GCA TAC CCG TAC GAC GTT CCG GAC TAC GCT AGC GGA TCC TAG TAG
 H   H   H   H   H   G   A   Y   P   Y   D   V   P   D   Y   A   S   G   S   -   -
```

Verotoxin-pA
(SEQ ID NOS: 29 and 30)
```
GGT ACC GCA TCC GGC AGC GCC TGC TCC CTG TGG GAC ACC ACA GGC TGG TGT CTG CAG GGT GGC GGC
 G   T   A   S   G   S   A   C   S   L   W   D   T   T   G   W   C   L   Q   G   G   G
TCT GGA GGC GGC AGT ACG CCT GAT TGT GTA ACT GGA AAG GTG GAG TAT ACA AAA TAT AAT GAT GAC
 S   G   G   G   S   T   P   D   C   V   T   G   K   V   E   Y   T   K   Y   N   D   D
GAT ACC TTT ACA GTT AAA GTG GGT GAT AAA GAA TTA TTT ACC AAC AGA TGG AAT CTT CAG TCT CTT
 D   T   F   T   V   K   V   G   D   K   E   L   F   T   N   R   W   N   L   Q   S   L
CTT CTC AGT GCG CAA ATT ACG GGG ATG ACT GTA ACC ATT AAA ACT AAT GCC TGT CAT AAT GGA GGG
 L   L   S   A   Q   I   T   G   M   T   V   T   I   K   T   N   A   C   H   N   G   G
GGA TTC AGC GAA GTT ATT TTT CGT GGC CAG GCC GGC CAG CAC CAT CAC CAT CAC CAC GGC GCA TAC
 G   F   S   E   V   I   F   R   G   Q   A   G   Q   H   H   H   H   H   H   G   A   Y
CCG TAC GAC GTT CCG GAC TAC GCT AGC GGA TCC TAG TAG
 P   Y   D   V   P   D   Y   A   S   G   S   -   -
```

Verotoxin-pA9
(SEQ ID NOS: 31 and 32)
```
GGT ACC GCA TCC GGC AGC GCC TGT CCG TCG TCG AGG TGG TTT GAT TTG TGT CTG CAG GGT GGC GGC
 G   T   A   S   G   S   A   C   P   S   S   R   W   F   D   L   C   L   Q   G   G   G
TCT GGA GGT GGC AGT ACG CCT GAT TGT GTA ACT GGA AAG GTG GAG TAT ACA AAA TAT AAT GAT GAC
 S   G   G   G   S   T   P   D   C   V   T   G   K   V   E   Y   T   K   Y   N   D   D
GAT ACC TTT ACA GTT AAA GTG GGT GAT AAA GAA TTA TTT ACC AAC AGA TGG AAT CTT CAG TCT CTT
 D   T   F   T   V   K   V   G   D   K   E   L   F   T   N   R   W   N   L   Q   S   L
CTT CTC AGT GCG CAA ATT ACG GGG ATG ACT GTA ACC ATT AAA ACT AAT GCC TGT CAT AAT GGA GGG
 L   L   S   A   Q   I   T   G   M   T   V   T   I   K   T   N   A   C   H   N   G   G
```

| Recombinant nanopeptamer subunits (protein subunit sequence is underlined) |
|---|
| GGA TTC AGC GAA GTT ATT TTT CGT GGC CAG GCC GGC CAG CAC CAT CAC CAT CAC CAC GGC GCA TAC |
| <u>G</u>  <u>F</u>  <u>S</u>  <u>E</u>  <u>V</u>  <u>I</u>  <u>F</u>  <u>R</u>  G  Q  A  G  Q  H  H  H  H  H  H  G  A  Y |
| CCG TAC GAC GTT CCG GAC TAC GCT AGC GGA TCC TAG TAG |
| P  Y  D  V  P  D  Y  A  S  G  S  -  - |

What is claimed is:

1. A method for non-competitive detection of a small analyte, the method comprising:
   (a) contacting at least one immune complex comprising an antibody specifically bound to the analyte, with an affinity agent comprising a self-associated oligomeric protein displaying multiple copies of a peptide, wherein at least one copy of the peptide specifically binds to the immune complex, and the peptide comprises from about 5 to about 50 amino acids; and
   (b) detecting the bound affinity agent, thereby detecting the analyte, where the analyte has a molecular weight of less than about 2500 daltons.

2. The method of claim 1, wherein the self-associated oligomeric protein is streptavidin, avidin, or verotoxin.

3. The method of claim 1, wherein the self-associated oligomeric protein is conjugated to a detectable label.

4. The method of claim 3, wherein the detectable label is an enzyme, a fluorescent label, a dye, or a magnetic particle.

5. The method of claim 1, wherein the peptide specifically binds to the immune complex.

6. The method of claim 1, wherein the peptide comprises from about 5 to about 25 amino acids.

7. The method of claim 1, wherein the peptide is obtained from a combinatorial biological or synthetic peptide library by selection with the analyte-antibody immune complex.

8. The method of claim 1, wherein the analyte has a molecular weight of less than about 1000 daltons.

9. The method of claim 1, wherein the analyte has a molecular weight of less than about 750 daltons.

10. The method of claim 1, wherein the analyte has a molecular weight of less than about 500 daltons.

11. The method of claim 1, further comprising contacting a sample suspected of containing the analyte with the antibody that specifically binds to the analyte, thereby forming the immune complex.

12. The method of claim 1, wherein the peptide is non-covalently attached to the self-associated oligomeric protein.

13. The method of claim 1, wherein the peptide is covalently attached to the self-associated oligomeric protein.

14. The method of claim 1, wherein the self-associated oligomeric protein comprises a plurality of subunit monomers each linked to a copy of the peptide.

15. The method of claim 14, wherein each subunit monomer is linked to the peptide by a peptide bond.

16. The method of claim 14, wherein each subunit monomer is linked to the peptide by a spacer comprising at least one amino acid.

17. A device for detecting a small analyte, the device comprising: (a) a solid support comprising an antibody that specifically binds to the analyte immobilized thereon; and (b) an affinity agent comprising a self-associated oligomeric protein displaying multiple copies of a peptide, the peptide comprising from about 5 to about 50 amino acids, wherein each peptide is capable of specifically binding to an immune complex formed when the antibody binds to the analyte, where the analyte has a molecular weight of less than about 2500 daltons.

18. The device of claim 17, wherein the self-associated oligomeric protein is conjugated to a detectable label.

19. The device of claim 18, wherein the detectable label is detectable by the human eye.

20. The device of claim 19, wherein the detectable label is a dye.

21. The device of claim 17, wherein the affinity agent is immobilized on the solid support.

* * * * *

SEQUENCE LISTING

```
<160> NUMBER OF SEQ ID NOS: 32

<210> SEQ ID NO 1
<211> LENGTH: 14
<212> TYPE: PRT
<213> ORGANISM: Artificial Sequence
<220> FEATURE:
<223> OTHER INFORMATION: synthetic immune complex specific biotinylated
      peptide A (pA), biotinylated anti-molinate IC peptide,
      biotinylated peptide A specific for anti-molinate monoclonal
      antibody MoAb 14D7-molinate immune complex (IC)
<221> NAME/KEY: MOD_RES
<222> LOCATION: (1)...(1)
<223> OTHER INFORMATION: Ser modified by biotin
<221> NAME/KEY: PEPTIDE
<222> LOCATION: (1)...(4)
<223> OTHER INFORMATION: spacer between biotin and anti-IC peptide
<221> NAME/KEY: PEPTIDE
<222> LOCATION: (5)...(14)
<223> OTHER INFORMATION: peptide A

<400> SEQUENCE: 1

Ser Gly Ser Gly Cys Ser Leu Trp Asp Thr Thr Gly Trp Cys
1               5                   10

<210> SEQ ID NO 2
<211> LENGTH: 14
<212> TYPE: PRT
<213> ORGANISM: Artificial Sequence
<220> FEATURE:
<223> OTHER INFORMATION: synthetic biotinylated immune complex specific
      peptide 1M (p1M), biotinylated anti-molinate IC peptide,
      biotinylated peptide 1M specific for anti-molinate monoclonal
      antibody MoAb 14D7-molinate immune complex (IC)
<220> FEATURE:
<221> NAME/KEY: MOD_RES
<222> LOCATION: (1)...(1)
<223> OTHER INFORMATION: Ser modified by biotin
<220> FEATURE:
<221> NAME/KEY: PEPTIDE
<222> LOCATION: (1)...(4)
<223> OTHER INFORMATION: spacer between biotin and anti-IC peptide
<220> FEATURE:
<221> NAME/KEY: PEPTIDE
<222> LOCATION: (5)...(14)
<223> OTHER INFORMATION: peptide 1M

<400> SEQUENCE: 2

Ser Gly Ser Gly Cys Ser Thr Trp Asp Thr Thr Gly Trp Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: synthetic biotinylated immune complex specific
      peptide ICX11 (pICX11), biotinylated anti-clomazone IC peptide,
      biotinylated peptide ICX11 specific for anti-clomazone monoclonal
      antibody MoAb 5.6-clomazone immune complex (IC)
<220> FEATURE:
<221> NAME/KEY: MOD_RES
```

```
<222> LOCATION: (1)...(1)
<223> OTHER INFORMATION: Ser modified by biotin
<220> FEATURE:
<221> NAME/KEY: PEPTIDE
<222> LOCATION: (1)...(4)
<223> OTHER INFORMATION: spacer between biotin and anti-IC peptide
<220> FEATURE:
<221> NAME/KEY: PEPTIDE
<222> LOCATION: (5)...(14)
<223> OTHER INFORMATION: peptide ICX11

<400> SEQUENCE: 3

Ser Gly Ser Gly Cys Leu Glu Ala Pro Asn Ile Glu Gly Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: synthetic immune complex specific peptide A
      (pA), anti-molinate IC peptide, peptide A specific for
      anti-molinate monoclonal antibody MoAb 14D7-molinate
      immune complex (IC)

<400> SEQUENCE: 4

Cys Ser Leu Trp Asp Thr Thr Gly Trp Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthetic immune complex specific peptide 1M
      (p1M), anti-molinate IC peptide, peptide 1M specific for
      anti-molinate monoclonal antibody MoAb 14D7-molinate
      immune complex (IC)

<400> SEQUENCE: 5

Cys Ser Thr Trp Asp Thr Thr Gly Trp Cys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: synthetic immune complex specific peptide
      ICX11 (pICX11), anti-clomazone IC peptide, peptide ICX11
      specific for anti-clomazone monoclonal antibody
      MoAb 5.6-clomazone immune complex (IC)

<400> SEQUENCE: 6

Cys Leu Glu Ala Pro Asn Ile Glu Gly Cys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: synthetic peptide A9 (pA9), anti-atrazine IC
      peptide, peptide A9 specific for anti-atrazine
      monoclonal antibody MoAb K4E7-atrazine immune
      complex (IC)

<400> SEQUENCE: 7

Cys Pro Ser Ser Arg Trp Phe Asp Leu Cys
1               5                   10
```

<210> SEQ ID NO 8
<211> LENGTH: 100
<212> TYPE: DNA
<213> ORGANISM: Artificial Sequence
<220> FEATURE:
<223> OTHER INFORMATION: synthetic PCR amplification primer A forward
      for Streptomyces avidinii streptavidin-peptide chimera
      construction

<400> SEQUENCE: 8
aaaaaaggcc caggcggccg gaggctgtct ggaggcgccg aacattgaag gctgcggtgg    60
cggctctgga ggtggcagtg ccgccgaagc cggcatcacg                         100

<210> SEQ ID NO 9
<211> LENGTH: 33
<212> TYPE: PRT
<213> ORGANISM: Artificial Sequence
<220> FEATURE:
<223> OTHER INFORMATION: synthetic translation of PCR amplification
      primer A forward for Streptomyces avidinii
      streptavidin-peptide chimera construction

<400> SEQUENCE: 9

Lys Lys Ala Gln Ala Ala Gly Gly Cys Leu Glu Ala Pro Asn Ile Glu
 1               5                  10                  15

Gly Cys Gly Gly Gly Ser Gly Gly Gly Ser Ala Ala Glu Ala Gly Ile
            20                  25                  30

Thr

<210> SEQ ID NO 10
<211> LENGTH: 8
<212> TYPE: PRT
<213> ORGANISM: Artificial Sequence
<220> FEATURE:
<223> OTHER INFORMATION: synthetic (G-3S)-2 spacer

<400> SEQUENCE: 10

Gly Gly Gly Ser Gly Gly Gly Ser
 1               5

<210> SEQ ID NO 11
<211> LENGTH: 112
<212> TYPE: DNA
<213> ORGANISM: Artificial Sequence
<220> FEATURE:
<223> OTHER INFORMATION: synthetic PCR amplification primer B forward
      for Streptomyces avidinii streptavidin-peptide chimera
      construction

<400> SEQUENCE: 11
tttaaaggcc caggcggccg catccggcag cgcctgctcc ctgtgggaca ccacaggctg    60
gtgtggccct cctcctcctc ctcctggcgc cgccgaagcc ggcatcacgg gc           112

<210> SEQ ID NO 12
<211> LENGTH: 37
<212> TYPE: PRT
<213> ORGANISM: Artificial Sequence
<220> FEATURE:
<223> OTHER INFORMATION: synthetic translation of PCR amplification
      primer B forward for Streptomyces avidinii
      streptavidin-peptide chimera construction

<400> SEQUENCE: 12

Leu Lys Ala Gln Ala Ala Ala Ser Gly Ser Ala Cys Ser Leu Trp Asp

```
              1               5                  10                 15
Thr Thr Gly Trp Cys Gly Pro Pro Pro Pro Pro Gly Ala Ala Glu
              20                 25                 30
Ala Gly Ile Thr Gly
              35
```

<210> SEQ ID NO 13
<211> LENGTH: 5
<212> TYPE: PRT
<213> ORGANISM: Artificial Sequence
<220> FEATURE:
<223> OTHER INFORMATION: synthetic ASGSA spacer

<400> SEQUENCE: 13

```
Ala Ser Gly Ser Ala
 1               5
```

<210> SEQ ID NO 14
<211> LENGTH: 8
<212> TYPE: PRT
<213> ORGANISM: Artificial Sequence
<220> FEATURE:
<223> OTHER INFORMATION: synthetic GP-6G spacer

<400> SEQUENCE: 14

```
Gly Pro Pro Pro Pro Pro Pro Gly
 1               5
```

<210> SEQ ID NO 15
<211> LENGTH: 40
<212> TYPE: DNA
<213> ORGANISM: Artificial Sequence
<220> FEATURE:
<223> OTHER INFORMATION: synthetic PCR amplification primer C reverse
      for Streptomyces avidinii streptavidin-peptide chimera
      construction

<400> SEQUENCE: 15
gttaaaccgt ctgccgcgtc cggccaggcc ggcctttttt                           40

<210> SEQ ID NO 16
<211> LENGTH: 13
<212> TYPE: PRT
<213> ORGANISM: Artificial Sequence
<220> FEATURE:
<223> OTHER INFORMATION: synthetic translation of PCR amplification
      primer C reverse for Streptomyces avidinii
      streptavidin-peptide chimera construction

<400> SEQUENCE: 16

```
Val Lys Pro Ser Ala Ala Ser Gly Gln Ala Gly Leu Phe
 1               5                  10
```

<210> SEQ ID NO 17
<211> LENGTH: 6
<212> TYPE: PRT
<213> ORGANISM: Artificial Sequence
<220> FEATURE:
<223> OTHER INFORMATION: synthetic His6-tag, histidine tail

<400> SEQUENCE: 17

```
His His His His His His
 1               5
```

<210> SEQ ID NO 18
<211> LENGTH: 66

```
<212> TYPE: DNA
<213> ORGANISM: Artificial Sequence
<220> FEATURE:
<223> OTHER INFORMATION: synthetic OmpA signal sequence and SfiI (1)
      site from pET-OmpA expresssion vector

<400> SEQUENCE: 18
atgaaaaaga cagctatcgc gattgcagtg gcactggctg gtttcgctac cgtggcccag    60
gcggcc                                                               66

<210> SEQ ID NO 19
<211> LENGTH: 87
<212> TYPE: DNA
<213> ORGANISM: Artificial Sequence
<220> FEATURE:
<223> OTHER INFORMATION: synthetic SfiI (2) site, His6-tag, HA epitope,
      BamHI, 2 stop codons and XhoI site from pET-OmpA
      expresssion vector

<400> SEQUENCE: 19
ggccaggccg gccagcacca tcaccatcac cacggcgcat acccgtacga cgttccggac    60
tacgctagcg gatcctagta gctcgag                                        87

<210> SEQ ID NO 20
<211> LENGTH: 207
<212> TYPE: DNA
<213> ORGANISM: Enterobacteria phage H-19B
<220> FEATURE:
<223> OTHER INFORMATION: verotoxin 1 B subunit (VT1B subunit), Shiga-
      like toxin I subunit B (slt1B)

<400> SEQUENCE: 20
acgcctgatt gtgtaactgg aaaggtggag tatacaaaat ataatgatga cgataccttt    60
acagttaaag tgggtgataa agaattattt accaacagat ggaatcttca gtctcttctt   120
ctcagtgcgc aaattacggg gatgactgta accattaaaa ctaatgcctg tcataatgga   180
gggggattca gcgaagttat ttttcgt                                       207

<210> SEQ ID NO 21
<211> LENGTH: 314
<212> TYPE: DNA
<213> ORGANISM: Artificial Sequence
<220> FEATURE:
<223> OTHER INFORMATION: synthetic verotoxin-pA chimera

<400> SEQUENCE: 21 ggccaggcg gccggtaccg catccggcag cgcctgctcc ctgtgggaca ccacaggctg     60
gtgtctgcag ggtggcggct ctggaggtgg cagtacgcct gattgtgtaa ctggaaaggt   120
ggagtataca aaatataatg atgacgatac ctttacagtt aaagtgggtg ataaagaatt   180
atttaccaac agatggaatc ttcagtctct tcttctcagt gcgcaaatta cggggatgac   240
tgtaaccatt aaaactaatg cctgtcataa tggaggggga ttcagcgaag ttattttcg   300 tggccaggcc ggcc                                                     314

<210> SEQ ID NO 22
<211> LENGTH: 104
<212> TYPE: PRT
<213> ORGANISM: Artificial Sequence
<220> FEATURE:
<223> OTHER INFORMATION: synthetic verotoxin-pA chimera

<400> SEQUENCE: 22
```

Ala Gln Ala Ala Gly Thr Ala Ser Gly Ser Ala Cys Ser Leu Trp Asp
1               5                   10                  15

Thr Thr Gly Trp Cys Leu Gln Gly Gly Ser Gly Gly Gly Ser Thr
            20                  25                  30

Pro Asp Cys Val Thr Gly Lys Val Glu Tyr Thr Lys Tyr Asn Asp Asp
            35                  40                  45

Asp Thr Phe Thr Val Lys Val Gly Asp Lys Glu Leu Phe Thr Asn Arg
        50                  55                  60

Trp Asn Leu Gln Ser Leu Leu Ser Ala Gln Ile Thr Gly Met Thr
65                  70                  75                  80

Val Thr Ile Lys Thr Asn Ala Cys His Asn Gly Gly Phe Ser Glu
                85                  90                  95

Val Ile Phe Arg Gly Gln Ala Gly
                100

<210> SEQ ID NO 23
<211> LENGTH: 51
<212> TYPE: DNA
<213> ORGANISM: Artificial Sequence
<220> FEATURE:
<223> OTHER INFORMATION: synthetic primer D for verotoxin-pA9 chimera

<400> SEQUENCE: 23
cgcatccggc agcgcctgtc cgtcgtcgag gtggtttgat tgtgtctgc a         51

<210> SEQ ID NO 24
<211> LENGTH: 51
<212> TYPE: DNA
<213> ORGANISM: Artificial Sequence
<220> FEATURE:
<223> OTHER INFORMATION: synthetic primer E for verotoxin-pA9 chimera

<400> SEQUENCE: 24
gacacaaatc aaaccacctc gacgacggac aggcgctgcc ggatgcggta c         51

<210> SEQ ID NO 25
<211> LENGTH: 534
<212> TYPE: DNA
<213> ORGANISM: Artificial Sequence
<220> FEATURE:
<223> OTHER INFORMATION: synthetic streptavidin-pA nanopeptamer subunit

<400> SEQUENCE: 25
gcatccggca gcgcctgctc cctgtgggac accacaggct ggtgtggccc tcctcctcct      60
cctcctggcg ccgccgaagc cggcatcacg ggcacttggt acaaccagct gggtagcacc     120
tttattgtca ccgcgggcgc cgatgggggca ctgacaggta cctatgagag cgctgtgggc    180
aacgcagaga gccgctatgt gctgaccggg cgctatgatt ccgccccggc caccgatggt    240
tctggtacgg ccctgggttg acggtggct tggaagaata actatcgtaa cgcgcattcc    300
gccactacct ggtccggtca atatgtgggc ggggccgaag cacgtattaa tacccagtgg    360
ctgttaacct ctggtacgac cgaagccaac gcctggaaga gcaccctggt cggccatgat    420
acgtttacca aagttaaacc gtctgccgcg tccggccagg ccggccagca ccatcaccat    480
caccacggcg cataccccgta cgacgttccg gactacgcta gcggatccta gtag         534

<210> SEQ ID NO 26
<211> LENGTH: 176
<212> TYPE: PRT
<213> ORGANISM: Artificial Sequence
<220> FEATURE:

<223> OTHER INFORMATION: synthetic streptavidin-pA nanopeptamer subunit

<400> SEQUENCE: 26

```
Ala Ser Gly Ser Ala Cys Ser Leu Trp Asp Thr Thr Gly Trp Cys Gly
1               5                   10                  15
Pro Pro Pro Pro Pro Gly Ala Ala Glu Ala Gly Ile Thr Gly Thr
            20                  25                  30
Trp Tyr Asn Gln Leu Gly Ser Thr Phe Ile Val Thr Ala Gly Ala Asp
        35                  40                  45
Gly Ala Leu Thr Gly Thr Tyr Glu Ser Ala Val Gly Asn Ala Glu Ser
    50                  55                  60
Arg Tyr Val Leu Thr Gly Arg Tyr Asp Ser Ala Pro Ala Thr Asp Gly
65                  70                  75                  80
Ser Gly Thr Ala Leu Gly Trp Thr Val Ala Trp Lys Asn Asn Tyr Arg
                85                  90                  95
Asn Ala His Ser Ala Thr Thr Trp Ser Gly Gln Tyr Val Gly Gly Ala
            100                 105                 110
Glu Ala Arg Ile Asn Thr Gln Trp Leu Leu Thr Ser Gly Thr Thr Glu
        115                 120                 125
Ala Asn Ala Trp Lys Ser Thr Leu Val Gly His Asp Thr Phe Thr Lys
    130                 135                 140
Val Lys Pro Ser Ala Ala Ser Gly Gln Ala Gly Gln His His His His
145                 150                 155                 160
His His Gly Ala Tyr Pro Tyr Asp Val Pro Asp Tyr Ala Ser Gly Ser
                165                 170                 175
```

<210> SEQ ID NO 27
<211> LENGTH: 525
<212> TYPE: DNA
<213> ORGANISM: Artificial Sequence
<220> FEATURE:
<223> OTHER INFORMATION: synthetic streptavidin-pICX11 nanopeptamer subunit

<400> SEQUENCE: 27

```
ggaggctgtc tggaggcgcc gaacattgaa ggctgcggtg gcggctctgg aggtggcagt      60
gccgccgaag ccggcatcac gggcacttgg tacaaccagc tgggtagcac ctttattgtc     120
accgcgggcg ccgatggggc actgacaggt acctatgaga gcgctgtggg caacgcagag     180
agccgctatg tgctgaccgg cgctatgat tccgccccgg ccaccgatgg ttctggtacg      240
gccctgggtt ggacggtggc ttggaagaat aactatcgta acgcgcattc cgccactacc     300
tggtccggtc aatatgtggg cggggccgaa gcacgtatta atcccagtg gctgttaacc     360
tctggtacga ccgaagccaa cgcctggaag agcaccctgg tcggccatga tacgtttacc     420
aaagttaaac cgtctgccgc gtccggccag gccggccagc accatcacca tcaccacggc     480
gcatacccgt acgacgttcc ggactacgct agcggatcct agtag                    525
```

<210> SEQ ID NO 28
<211> LENGTH: 173
<212> TYPE: PRT
<213> ORGANISM: Artificial Sequence
<220> FEATURE:
<223> OTHER INFORMATION: synthetic streptavidin-pICX11 nanopeptamer subunit

<400> SEQUENCE: 28

```
Gly Gly Cys Leu Glu Ala Pro Asn Ile Glu Gly Cys Gly Gly Gly Ser
1               5                   10                  15
```

Gly Gly Gly Ser Ala Ala Glu Ala Gly Ile Thr Gly Thr Trp Tyr Asn
            20                  25                  30

Gln Leu Gly Ser Thr Phe Ile Val Thr Ala Gly Ala Asp Gly Ala Leu
            35                  40                  45

Thr Gly Thr Tyr Glu Ser Ala Val Gly Asn Ala Glu Ser Arg Tyr Val
 50                  55                  60

Leu Thr Gly Arg Tyr Asp Ser Ala Pro Ala Thr Asp Gly Ser Gly Thr
 65                  70                  75                  80

Ala Leu Gly Trp Thr Val Ala Trp Lys Asn Asn Tyr Arg Asn Ala His
             85                  90                  95

Ser Ala Thr Thr Trp Ser Gly Gln Tyr Val Gly Gly Ala Glu Ala Arg
            100                 105                 110

Ile Asn Thr Gln Trp Leu Leu Thr Ser Gly Thr Thr Glu Ala Asn Ala
            115                 120                 125

Trp Lys Ser Thr Leu Val Gly His Asp Thr Phe Thr Lys Val Lys Pro
130                 135                 140

Ser Ala Ala Ser Gly Gln Ala Gly Gln His His His His His His Gly
145                 150                 155                 160

Ala Tyr Pro Tyr Asp Val Pro Asp Tyr Ala Ser Gly Ser
                165                 170

<210> SEQ ID NO 29
<211> LENGTH: 369
<212> TYPE: DNA
<213> ORGANISM: Artificial Sequence
<220> FEATURE:
<223> OTHER INFORMATION: synthetic verotoxin-pA nanopeptamer subunit

<400> SEQUENCE: 29
ggtaccgcat ccggcagcgc ctgctccctg tgggacacca caggctggtg tctgcagggt       60
ggcggctctg gaggtggcag tacgcctgat tgtgtaactg gaaaggtgga gtatacaaaa      120
tataatgatg acgataccct tacagttaaa gtgggtgata agaattatt taccaacaga      180 tggaatcttc agtctcttct tctcagtgcg caaattacgg ggatgactgt aaccattaaa     240
actaatgcct gtcataatgg aggggattc agcgaagtta ttttcgtgg ccaggccggc      300 cagcaccatc accatcacca cggcgcatac ccgtacgacg ttccggacta cgctagcgga      360
tcctagtag                                                              369

<210> SEQ ID NO 30
<211> LENGTH: 121
<212> TYPE: PRT
<213> ORGANISM: Artificial Sequence
<220> FEATURE:
<223> OTHER INFORMATION: synthetic verotoxin-pA nanopeptamer subunit

<400> SEQUENCE: 30

Gly Thr Ala Ser Gly Ser Ala Cys Ser Leu Trp Asp Thr Thr Gly Trp
  1               5                  10                  15

Cys Leu Gln Gly Gly Gly Ser Gly Gly Gly Ser Thr Pro Asp Cys Val
             20                  25                  30

Thr Gly Lys Val Glu Tyr Thr Lys Tyr Asn Asp Asp Thr Phe Thr
             35                  40                  45

Val Lys Val Gly Asp Lys Glu Leu Phe Thr Asn Arg Trp Asn Leu Gln
 50                  55                  60

Ser Leu Leu Leu Ser Ala Gln Ile Thr Gly Met Thr Val Thr Ile Lys
 65                  70                  75                  80

```
Thr Asn Ala Cys His Asn Gly Gly Phe Ser Glu Val Ile Phe Arg
            85                  90                  95

Gly Gln Ala Gly Gln His His His His His Gly Ala Tyr Pro Tyr
                100                 105                 110

Asp Val Pro Asp Tyr Ala Ser Gly Ser
        115                 120

<210> SEQ ID NO 31
<211> LENGTH: 369
<212> TYPE: DNA
<213> ORGANISM: Artificial Sequence
<220> FEATURE:
<223> OTHER INFORMATION: synthetic verotoxin-pA9 nanopeptamer subunit

<400> SEQUENCE: 31
ggtaccgcat ccggcagcgc ctgtccgtcg tcgaggtggt ttgatttgtg tctgcagggt      60
ggcggctctg gaggtggcag tacgcctgat tgtgtaactg gaaaggtgga gtatacaaaa    120
tataatgatg acgataccnt tacagttaaa gtgggtgata agaattatt taccaacaga    180 tggaatcttc agtctcttct tctcagtgcg caaattacgg ggatgactgt aaccattaaa    240
actaatgcct gtcataatgg agggggattc agcgaagtta ttttcgtgg ccaggccggc     300 cagcaccatc accatcacca cggcgcatac ccgtacgacg ttccggacta cgctagcgga    360
tcctagtag                                                             369

<210> SEQ ID NO 32
<211> LENGTH: 121
<212> TYPE: PRT
<213> ORGANISM: Artificial Sequence
<220> FEATURE:
<223> OTHER INFORMATION: synthetic verotoxin-pA9 nanopeptamer subunit

<400> SEQUENCE: 32

Gly Thr Ala Ser Gly Ser Ala Cys Pro Ser Ser Arg Trp Phe Asp Leu
1               5                   10                  15

Cys Leu Gln Gly Gly Gly Ser Gly Gly Gly Ser Thr Pro Asp Cys Val
            20                  25                  30

Thr Gly Lys Val Glu Tyr Thr Lys Tyr Asn Asp Asp Thr Phe Thr
        35                  40                  45

Val Lys Val Gly Asp Lys Glu Leu Phe Thr Asn Arg Trp Asn Leu Gln
    50                  55                  60

Ser Leu Leu Leu Ser Ala Gln Ile Thr Gly Met Thr Val Thr Ile Lys
65                  70                  75                  80

Thr Asn Ala Cys His Asn Gly Gly Phe Ser Glu Val Ile Phe Arg
            85                  90                  95

Gly Gln Ala Gly Gln His His His His His Gly Ala Tyr Pro Tyr
                100                 105                 110

Asp Val Pro Asp Tyr Ala Ser Gly Ser
        115                 120
```